(12) United States Patent
DelSpina

(10) Patent No.: US 10,099,368 B2
(45) Date of Patent: Oct. 16, 2018

(54) SYSTEM FOR CONTROLLING LIGHT AND FOR TRACKING TOOLS IN A THREE-DIMENSIONAL SPACE

(71) Applicant: Brandon DelSpina, Clemson, SC (US)

(72) Inventor: Brandon DelSpina, Clemson, SC (US)

(*) Notice: Subject to any disclaimer, the term of this patent is extended or adjusted under 35 U.S.C. 154(b) by 175 days.

(21) Appl. No.: 15/400,378

(22) Filed: Jan. 6, 2017

(65) Prior Publication Data

US 2018/0111265 A1  Apr. 26, 2018

Related U.S. Application Data

(60) Provisional application No. 62/412,593, filed on Oct. 25, 2016, provisional application No. 62/430,203, filed on Dec. 5, 2016.

(51) Int. Cl.
*B25J 9/00* (2006.01)
*B25J 9/16* (2006.01)
*G06T 7/70* (2017.01)
*G06F 3/01* (2006.01)
*H05B 37/02* (2006.01)
*A61B 34/20* (2016.01)
*F21V 21/15* (2006.01)
(Continued)

(52) U.S. Cl.
CPC ............ *B25J 9/161* (2013.01); *A61B 34/20* (2016.02); *G06F 3/011* (2013.01); *G06T 7/70* (2017.01); *H05B 37/0209* (2013.01); *A61B 2034/2057* (2016.02); *A61B 2034/2072* (2016.02); *F21S 8/061* (2013.01); *F21V 21/15* (2013.01); *F21V 21/16* (2013.01); *F21W 2131/205* (2013.01); *F21Y 2115/10* (2016.08); *G06T 2207/10016* (2013.01); *G06T 2207/30204* (2013.01)

(58) Field of Classification Search
USPC ................................... 700/245–264
See application file for complete search history.

(56) References Cited

U.S. PATENT DOCUMENTS 5,113,768 A * 5/1992 Brown .................... B61B 7/02
104/112
5,224,426 A * 7/1993 Rodnunsky ............. B61B 7/00
104/112

(Continued)

FOREIGN PATENT DOCUMENTS

CN  20397355  12/2014
DE  4201934  7/1993

(Continued)

*Primary Examiner* — Jonathan L Sample
(74) *Attorney, Agent, or Firm* — Pitts & Lake, P.C.

(57) ABSTRACT

A system adapted for supporting workflow in a three-dimensional space which provides, among other things, hands-free control and adjustment of lighting within the three-dimensional space. The system of the present invention is also adapted for delivering, tracking, and retrieving tools in the three-dimensional space. The system of the present invention includes various subsystems, which are referred to herein as modules, that both act independently and co-dependently, as will be described in greater detail below, in conjunction with a central control computer module. The modules consist, in an exemplary embodiment, of the cable robot module, the central computer module, the imaging module, the illumination module, and the object manipulator module.

46 Claims, 23 Drawing Sheets

(51) Int. Cl.
*F21V 21/16* (2006.01)
*F21S 8/06* (2006.01)
*F21W 131/205* (2006.01)
*F21Y 115/10* (2016.01)

(56) References Cited

U.S. PATENT DOCUMENTS

| | | | |
|---|---|---|---|
| 5,568,189 A * | 10/1996 | Kneller | H04N 5/222 |
| | | | 248/58 |
| 6,477,442 B1 | 11/2002 | Valerino, Sr. | |
| 6,826,452 B1 * | 11/2004 | Holland | B66C 1/663 |
| | | | 318/566 |
| 7,088,071 B2 * | 8/2006 | Rodnunsky | F16M 11/045 |
| | | | 104/180 |
| 7,151,848 B1 * | 12/2006 | Watanabe | B25J 9/1656 |
| | | | 382/141 |
| 7,207,277 B2 | 4/2007 | Rodnunsky | |
| 7,340,077 B2 | 3/2008 | Gokturk | |
| 7,606,411 B2 | 10/2009 | Venetsky | |
| 8,098,928 B2 | 1/2012 | Ban | |
| 8,199,197 B2 * | 6/2012 | Bennett | F16M 11/105 |
| | | | 348/144 |
| 8,418,662 B2 * | 4/2013 | Kim | F22B 37/003 |
| | | | 122/363 |
| 8,543,240 B2 | 9/2013 | Itkowitz | |
| 8,620,473 B2 | 12/2013 | Diolaiti | |
| 8,682,489 B2 | 3/2014 | Itkowitz | |
| 8,817,085 B2 | 8/2014 | Hiltl | |
| 8,824,802 B2 | 9/2014 | Kutliroff | |
| 8,866,781 B2 | 10/2014 | Li | |
| 8,996,173 B2 | 3/2015 | Itkowitz | |
| 9,063,390 B2 * | 6/2015 | Wharton | G03B 15/00 |
| 9,275,277 B2 | 3/2016 | Onen | |
| 9,337,949 B2 * | 5/2016 | Wharton | H04J 14/02 |
| 9,477,141 B2 * | 10/2016 | Wharton | H04N 5/2251 |
| 2001/0056313 A1 | 12/2001 | Osborne | |
| 2009/0103909 A1 * | 4/2009 | Giegerich | F16M 11/18 |
| | | | 396/12 |
| 2009/0207250 A1 * | 8/2009 | Bennett | F16M 11/105 |
| | | | 348/144 |
| 2010/0066676 A1 | 3/2010 | Kramer et al. | |
| 2013/0050069 A1 | 2/2013 | Ota | |
| 2013/0096575 A1 | 4/2013 | Olson | |
| 2013/0321613 A1 * | 12/2013 | Hansen | H04N 7/18 |
| | | | 348/84 |
| 2013/0345876 A1 * | 12/2013 | Rudakevych | B25J 9/1697 |
| | | | 700/259 |
| 2015/0062328 A1 * | 3/2015 | Lauffer | G06T 7/0004 |
| | | | 348/125 |
| 2015/0293596 A1 | 10/2015 | Krausen | |
| 2015/0375399 A1 | 12/2015 | Chiu | |
| 2016/0023761 A1 * | 1/2016 | McNally | B64C 39/024 |
| | | | 29/407.01 |
| 2017/0027803 A1 * | 2/2017 | Agrawal | A61B 5/6828 |

FOREIGN PATENT DOCUMENTS

| | | |
|---|---|---|
| DE | 20001134 | 6/2000 |
| DE | 102013110847 | 1/2015 |
| KR | 962526 | 3/2007 |

* cited by examiner

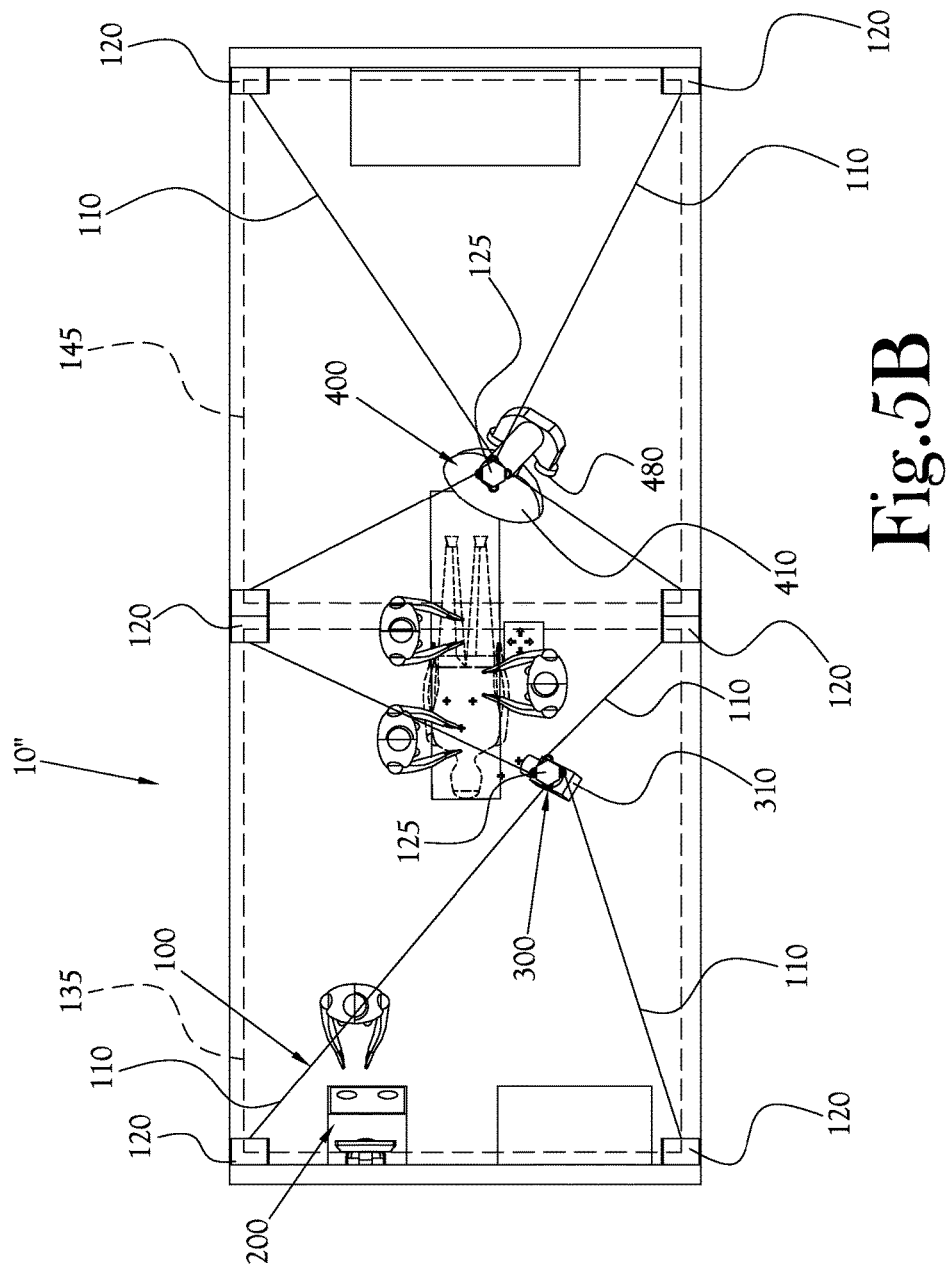

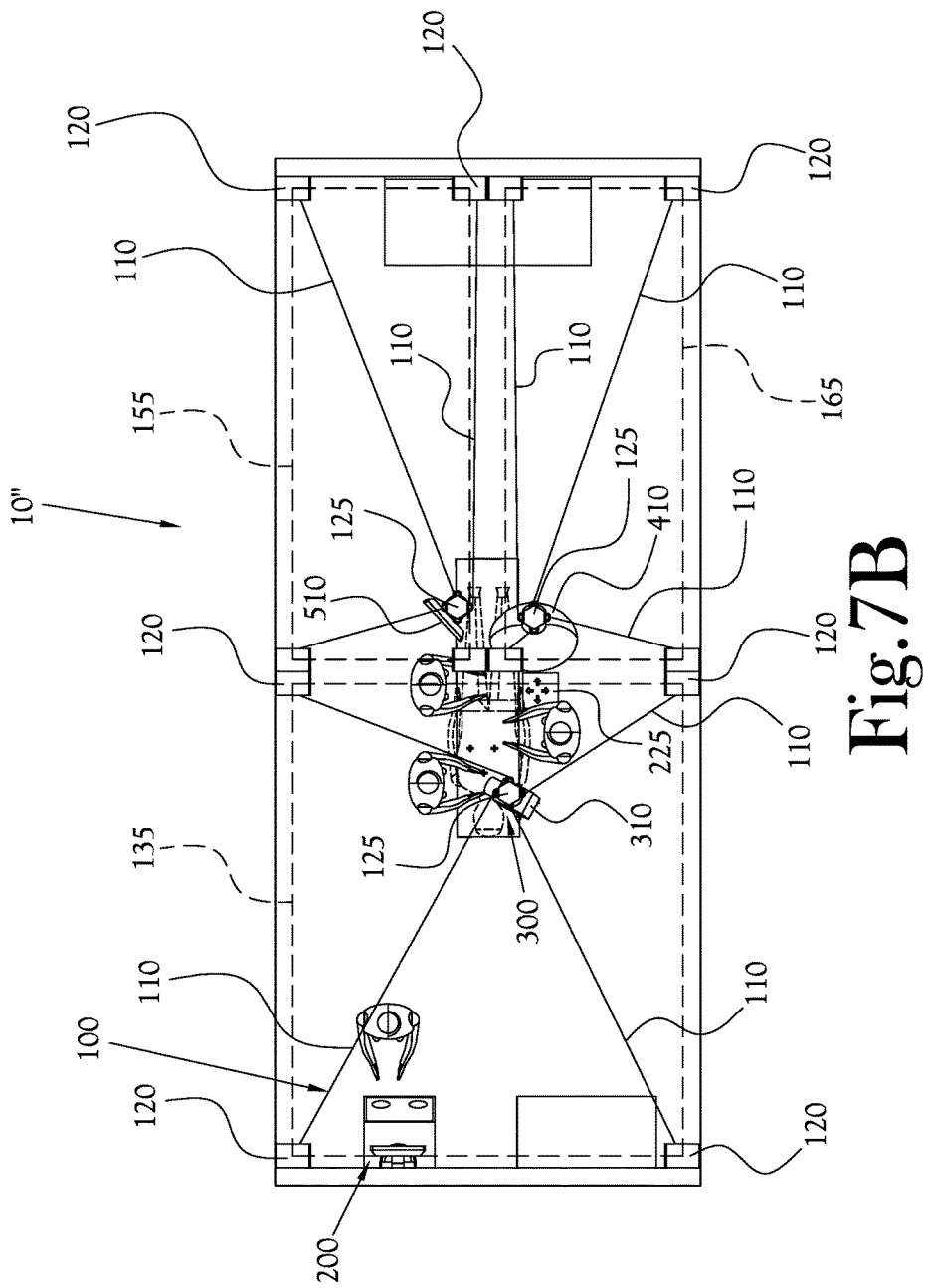

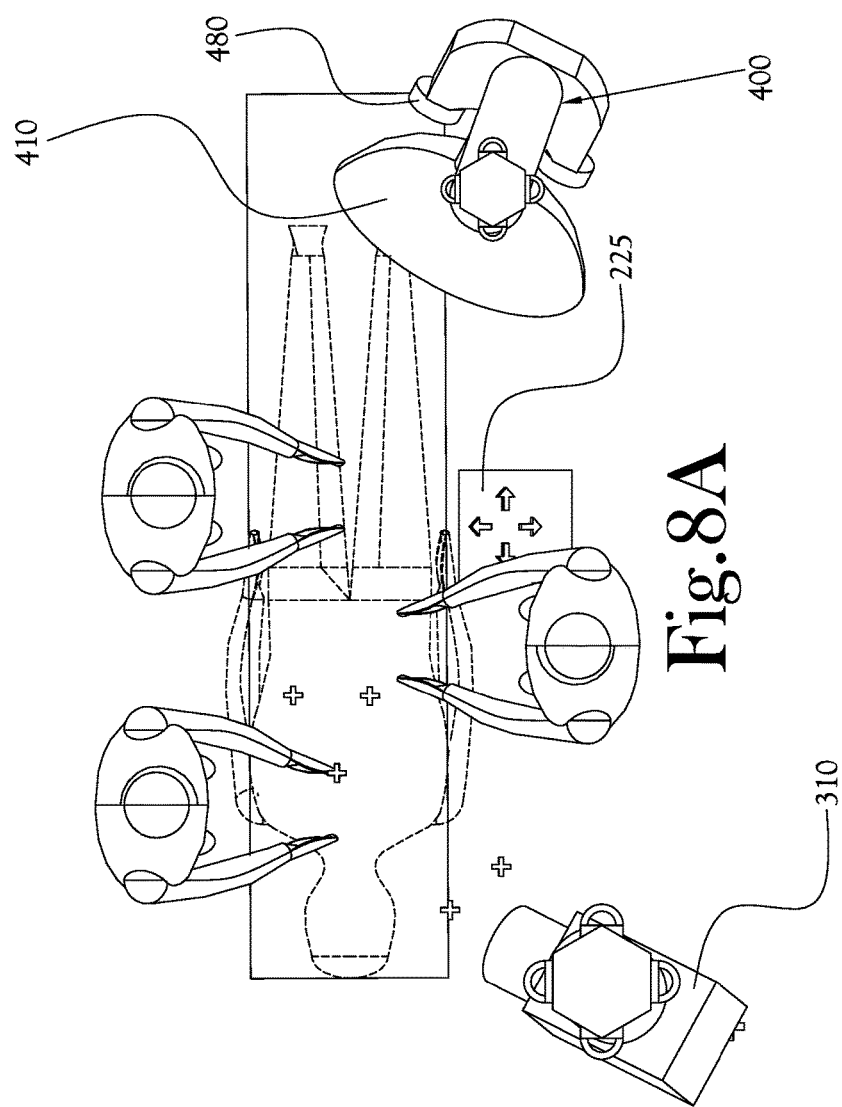

SYSTEM FOR CONTROLLING LIGHT AND FOR TRACKING TOOLS IN A THREE-DIMENSIONAL SPACE

CROSS-REFERENCE TO RELATED APPLICATIONS

This application claims the benefit of U.S. Provisional Patent Application No. 62/412,593, filed on Oct. 25, 2016, and U.S. Provisional Patent Application No. 62/430,203, filed on Dec. 5, 2016, each of which is incorporated herein in its entirety by reference.

STATEMENT REGARDING FEDERALLY SPONSORED RESEARCH OR DEVELOPMENT

Not Applicable

BACKGROUND OF THE INVENTION

1. Field of Invention

The invention relates to a system for controlling lighting, delivery and retrieval of selected tools, and tracking the position and orientation of such tools. More particularly, it relates to a system for supporting workflow, controlling light, and for tracking and delivering objects in a three-dimensional space, such as a medical surgical suite or operating theater.

2. Description of the Related Art

In the field of supporting the workflow of people, objects, and/or tools in a three-dimensional space, it is known that one such three-dimensional space in which it is particularly critical to manage lighting systems and environmental workflow is the modern medical surgical suite referred to herein as an operating theater. As used herein, "operating theater" refers to various medical, outpatient, or dental environments, including both hospital and clinical environments. With regards to such an operating theater, it is known that every minute of operating time is expensive, some reporting the cost as high as $19 per minute of operating time. It is also known that every seven and a half minutes, surgical suite, or operating theater, personnel adjust an illumination device; and that surgeons spend as much as one quarter of their time adjusting the lighting. And, for nearly two thirds of these lighting adjustments interrupt the surgical tasks of the operating room staff. Further, it will be understood by those skilled in the art that physical interaction with overhead booms and lighting equipment mounted on floor mounted booms requires continuous sterilization of at least the lighting equipment's handles. Further, those skilled in the art recognize that in environments having multiple light booms, there is a risk of light booms colliding with one another; further head-worn lamps cause headaches and do not necessarily point in the direction that the surgeon's eyes are looking. Moreover, conventional light booms are simply cumbersome.

It is also known in the art to utilize passive or active infrared signals, for example, the passive infrared spheres illustrated in FIG. 1, which can be placed on a rigid body, for example, the surgical tool illustrated in FIG. 2, for tracking the position and orientation of such a rigid body through six degrees of freedom, i.e. movement through the X, Y, and Z coordinates in three-dimensional space and movements such as roll, pitch, and yaw. This enables image guided surgery which in turn allows surgeons to accurately and precisely position surgical instruments in a way which avoids critical or sensitive body structures and yet accomplish the appropriate surgical task.

In view of the known art, there is a need for tool and treatment tracking during surgery and operation in clinical settings. Further, there is a need for increased efficiency in tool delivery to site of application from time of request. There is additionally, a need for greater illumination of the area of interest and its surroundings and better more efficient control of this lighting.

BRIEF SUMMARY OF THE INVENTION

The system of the present invention is adapted for supporting workflow in a three-dimensional space and provides, among other things, touchless control and adjustment of lighting within the three-dimensional space. The system of the present invention is also adapted for delivering, tracking, positioning, and retrieving tools in the three-dimensional space. The system of the present invention includes various subsystems, which are referred to herein as modules, that both act independently and co-dependently, as will be described in greater detail below, in conjunction with a central control computer module. The modules consist, in an exemplary embodiment, of the cable robot module, the central computer module, the imaging module and its vector camera, the illumination module, and the object manipulator module.

The present invention solves the needs described above by utilizing a system that incorporates a variety of subsystems, referred to herein as modules, to control and position a variety of tools including an imaging module, an illumination module, and an object manipulator module each module capable of acting independently of the other modules for controlling lighting and for delivering, tracking, and retrieving various objects and tools with greater precision, versatility and in a closer proximity than currently available. The system of the present invention utilizes a cable robot module for controlling the position and field of view of a vector camera, both under control of a central computer module. The system of the present invention includes a cable robot module composed of three or more cables attached to three or more points in a three-dimensional space, such as a room to rotate and translate one or more of the component modules from point of retrieval to point of delivery. Further, the system of the present invention can also incorporate an illumination module and/or an object manipulator module. It will be understood that the one or more of these systems can operate in a given three-dimensional space and can work both independently of each other and co-dependently with each other to ensure an efficient use of the three-dimensional space and to avoid collisions and entanglement issues.

BRIEF DESCRIPTION OF THE SEVERAL VIEWS OF THE DRAWINGS

The above-mentioned features of the invention will become more clearly understood from the following detailed description of the invention read together with the drawings in which:

FIGS. 5A and 5B are top plan views of the embodiment of the system illustrated in FIG. 4E illustrating two devices in simultaneous and independent operation in which each device's domain, or zone of operation, is illustrated schematically in FIG. 5B;

FIGS. 7A and 7B are top plan views of the embodiment of the system illustrated in FIG. 6A illustrating three devices in simultaneous and independent operation in which each device's domain, or zone of operation, is illustrated schematically in FIG. 7B;

FIG. 8A is a top plan view of a further exemplary embodiment of the system of the present invention in which operation of the system is directed by use of a foot controller operated by a clinician and in which cables have been removed for clarity of view;

DETAILED DESCRIPTION OF THE INVENTION

Figure 1:
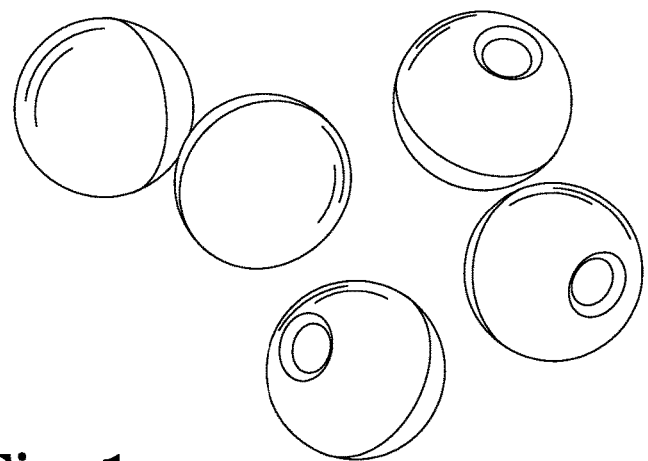
FIG. 1 is a perspective view of a prior art passive infrared (IR) sphere used for rigid body tracking.
Figure 2:
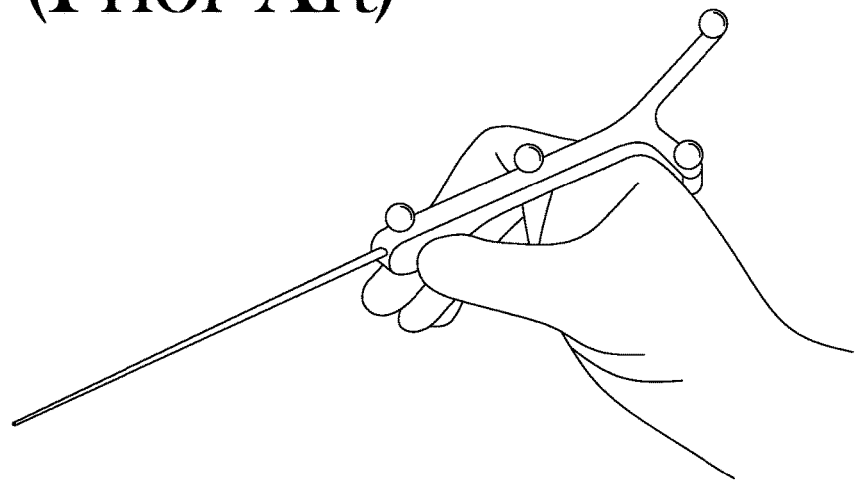
FIG. 2 is a perspective view of a prior art surgical tool having IR spheres, as illustrated in FIG. 1, attached for tool tracking.
Figure 3:
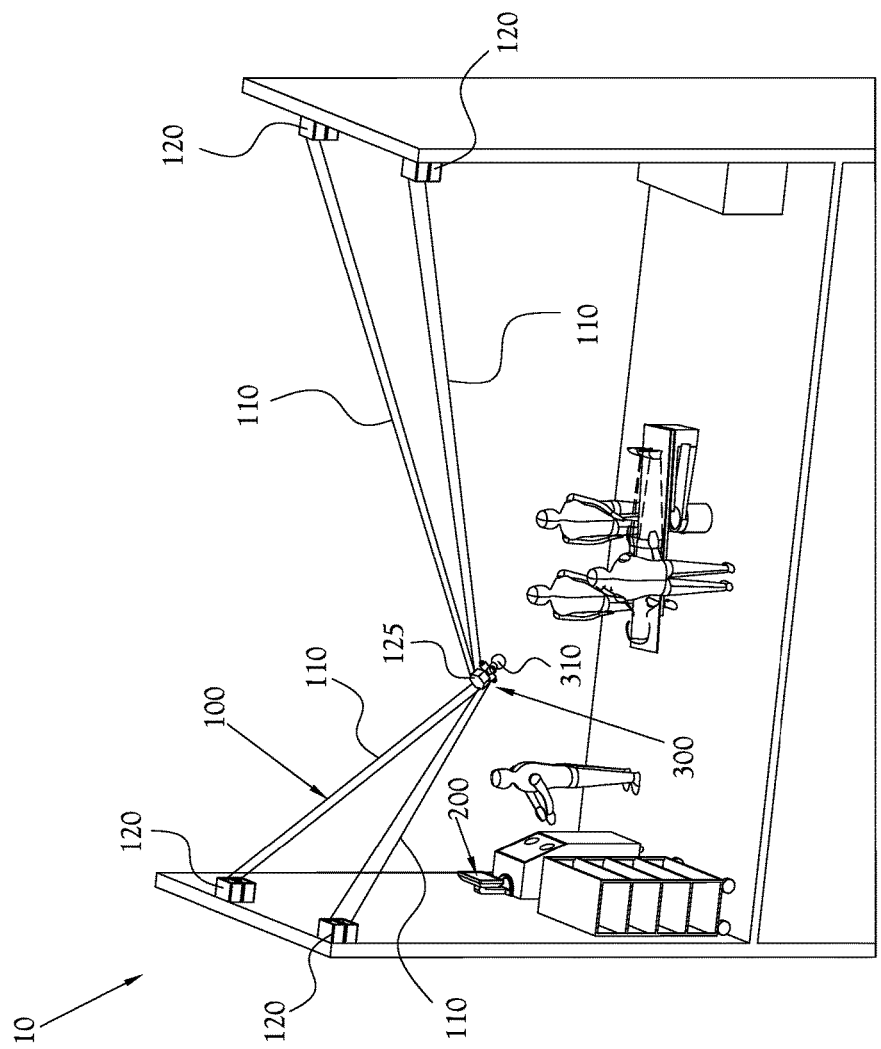
FIG. 3 is a perspective view of an exemplary embodiment of the system of the present invention as deployed in an operating theater.

FIGS. 3-10C illustrate a system 10 for controlling light and for delivering, tracking and/or retrieving tools in a three-dimensional space. System 10 includes various subsystems, referred to herein as modules, that act independently and co-dependently in conjunction with a central control computer. The modules consist, in an exemplary embodiment, of the cable robot module 100, the central computer module, represented schematically at 200, the imaging module 300, the illumination module 400, and the object manipulator module 500. In an exemplary embodiment, a cable robot module 100 can carry one or more of the imaging module 300, the illumination module 400, and/or the object manipulator module 500. For instance, in one exemplary embodiment, a single cable robot module 100 could carry, position, and reposition as necessary both an imaging module 300 and an illumination module 400. Further, as described in greater detail below, while a single cable robot module 100 could be utilized to carry one or more of the imaging module 300, the illumination module 400, and/or the object manipulator module 500, a plurality of cable robot modules 100 could be utilized to carry the other modules individually.

Figure 4A:
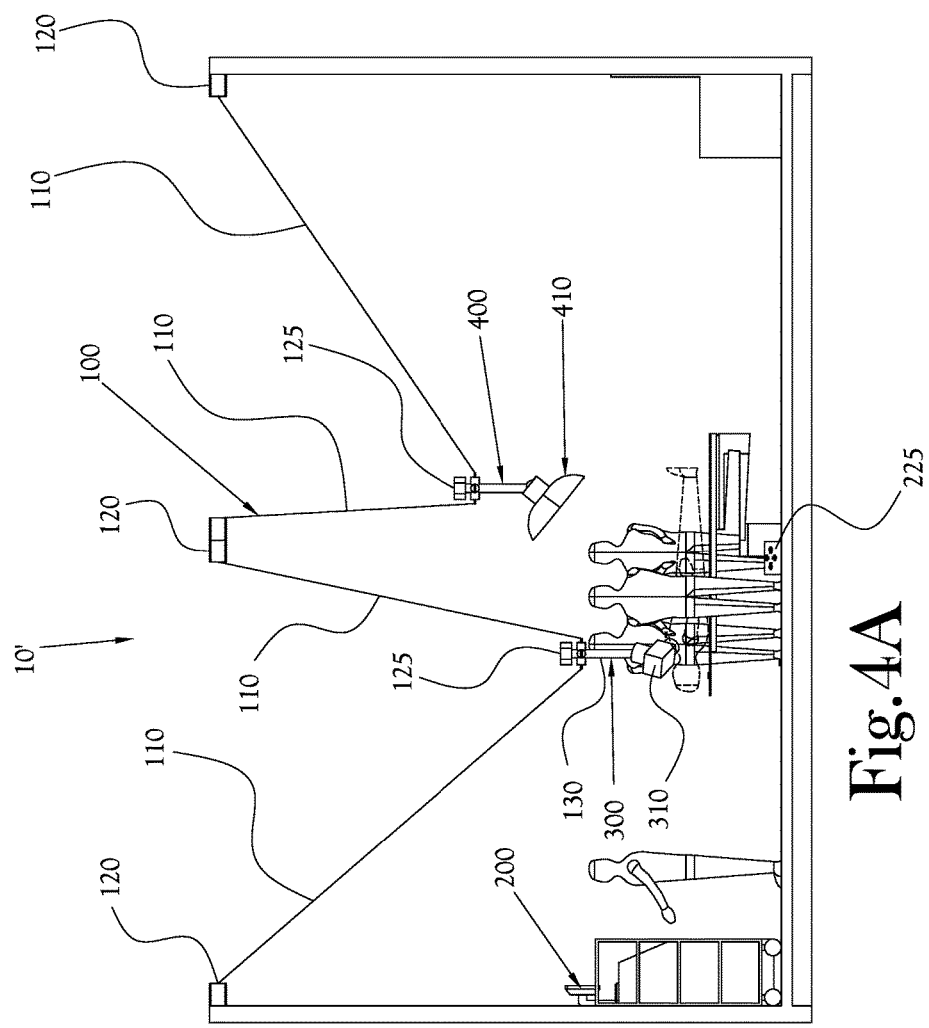
FIG. 4A is a side elevation view of a further exemplary embodiment of the system of the present invention as deployed in an operating theater.
Figure 4B:
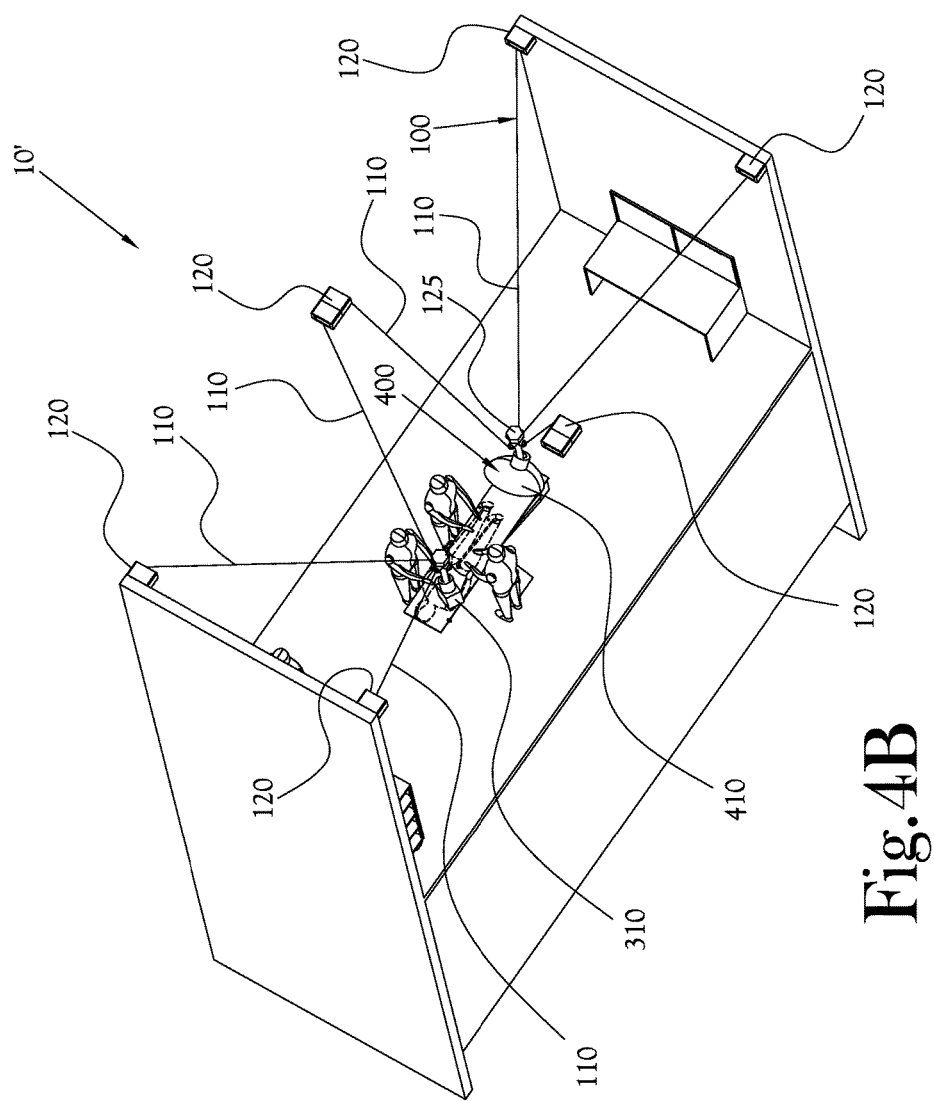
FIG. 4B is a perspective view of the embodiment of the system illustrated in FIG. 4A.
Figure 4C:
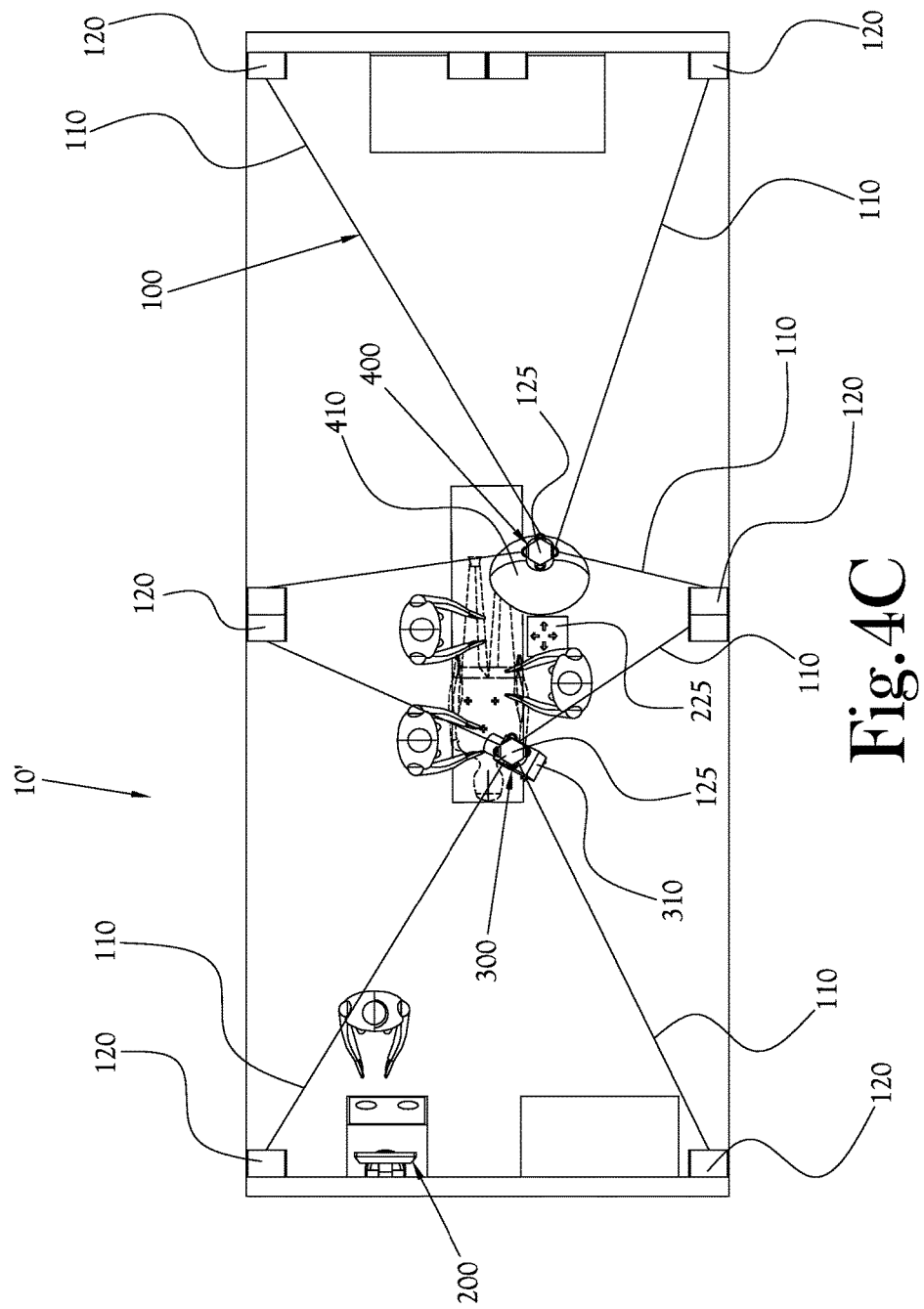
FIG. 4C is a top plan view of the embodiment of the system illustrated in FIG. 4A.
Figure 4D:
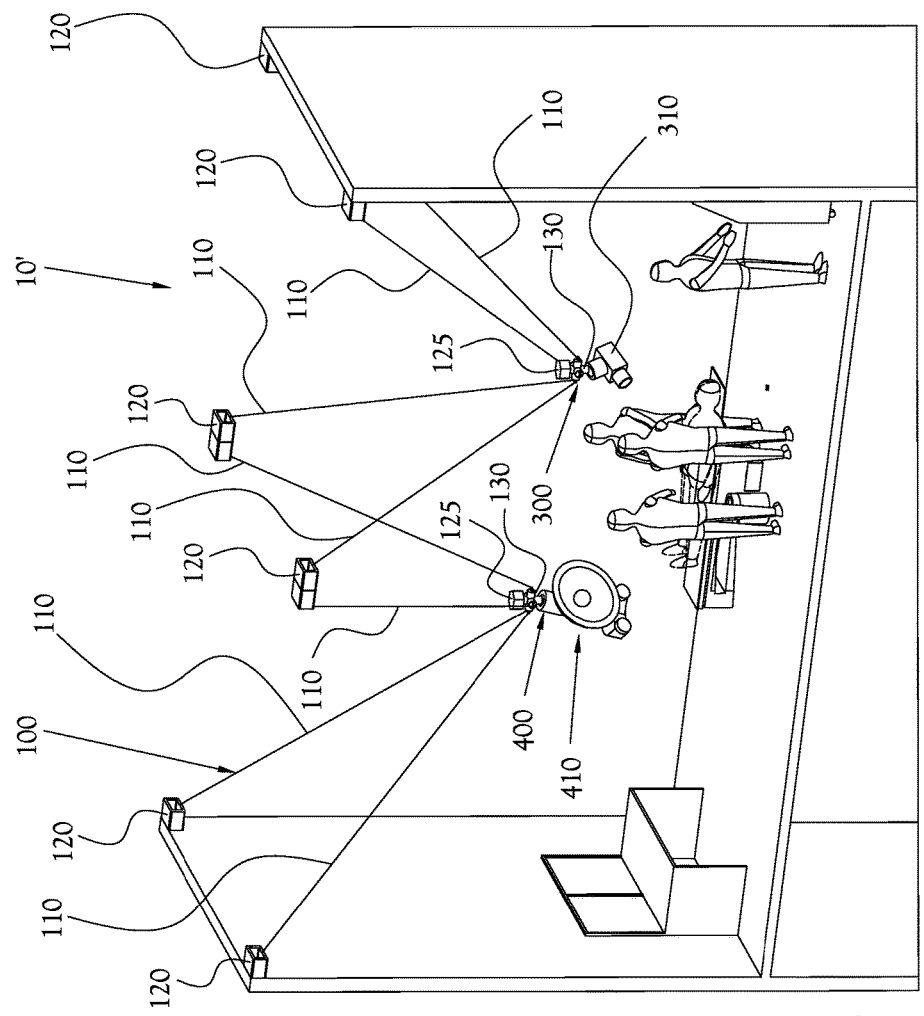
FIG. 4D is a further perspective view of the embodiment of the system illustrated in FIG. 4A.
Figure 4E:
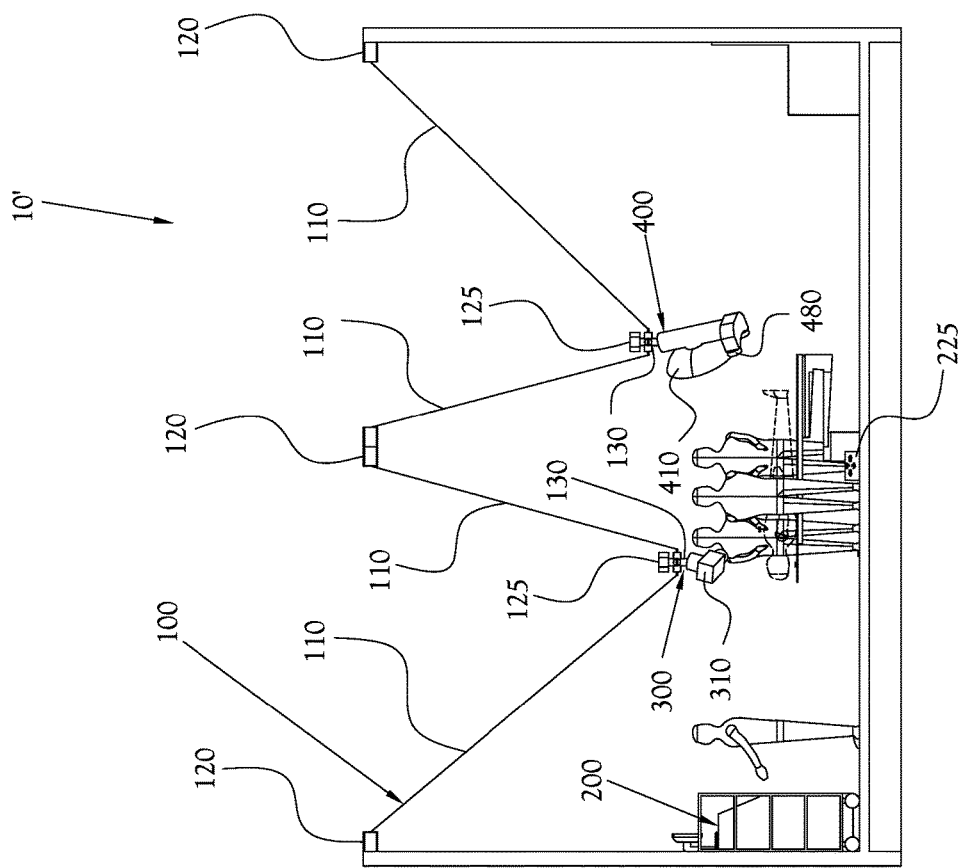
FIG. 4E is a right side elevation view of the embodiment of the system illustrated in FIG. 4A illustrating an alternate light source.
Figure 4F:
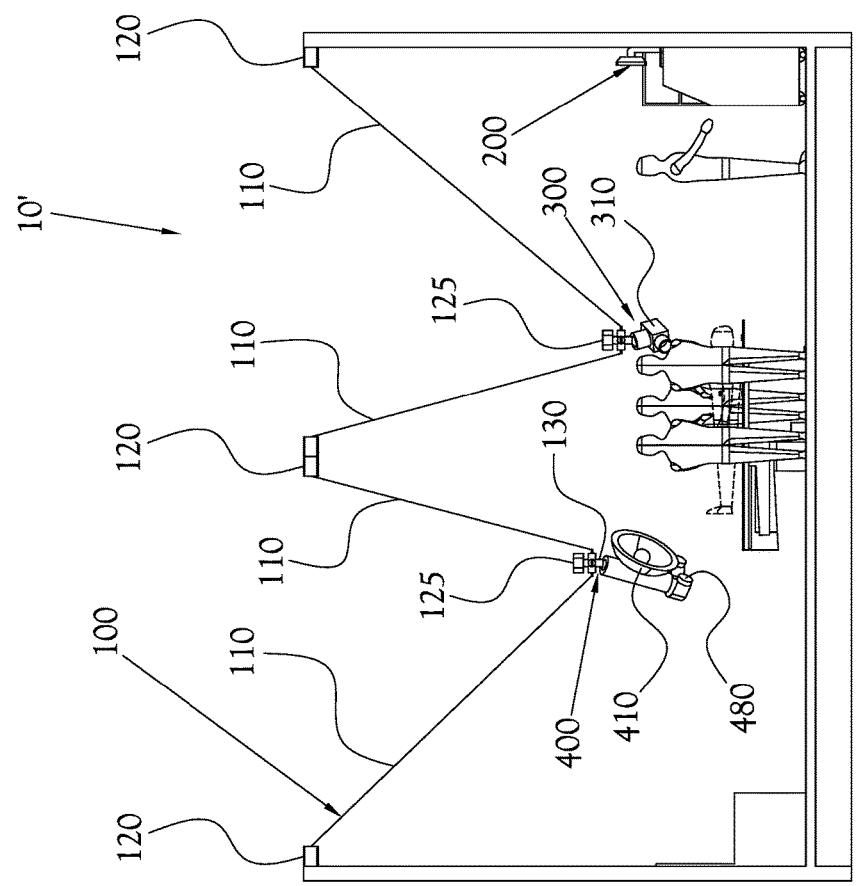
FIG. 4F is left side elevation view of the embodiment of the system illustrated in FIG. 4E.
Figure 5A:
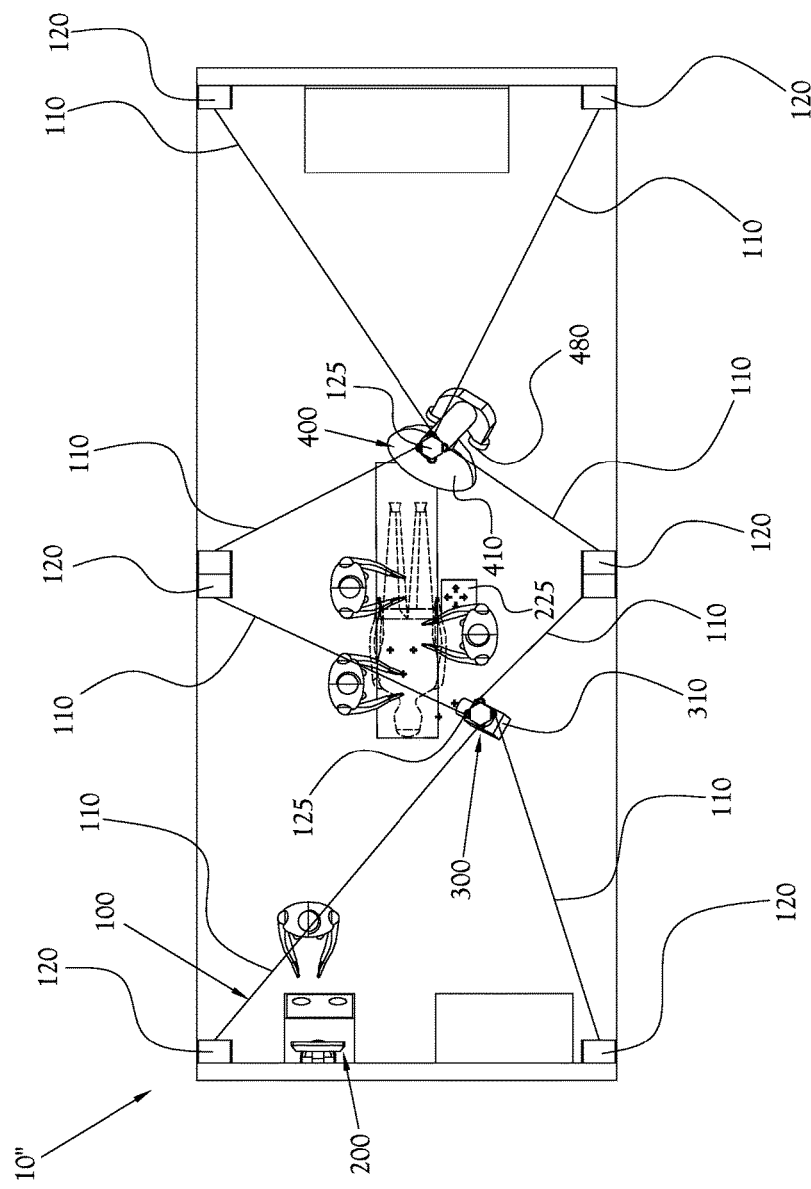
Figure 6A:
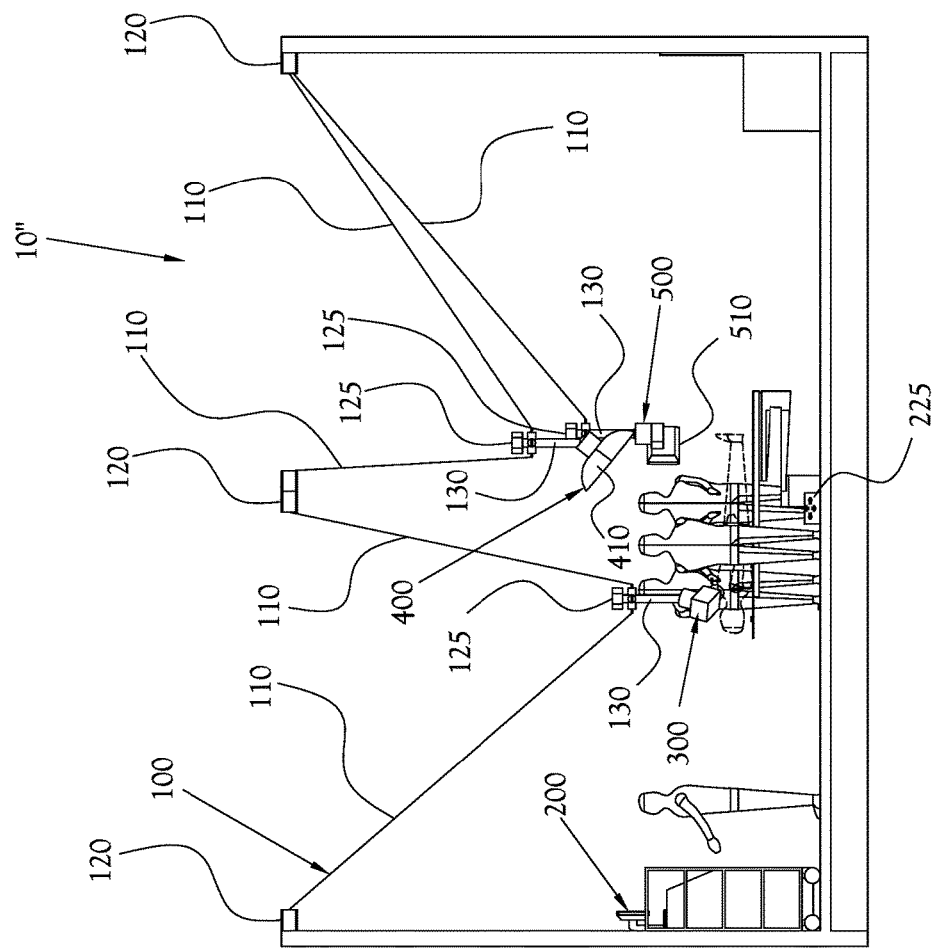
FIG. 6A is a side elevation view of a further exemplary embodiment of the system of the present invention illustrating a three cable system for operating three devices independently and simultaneously.
Figure 6B:
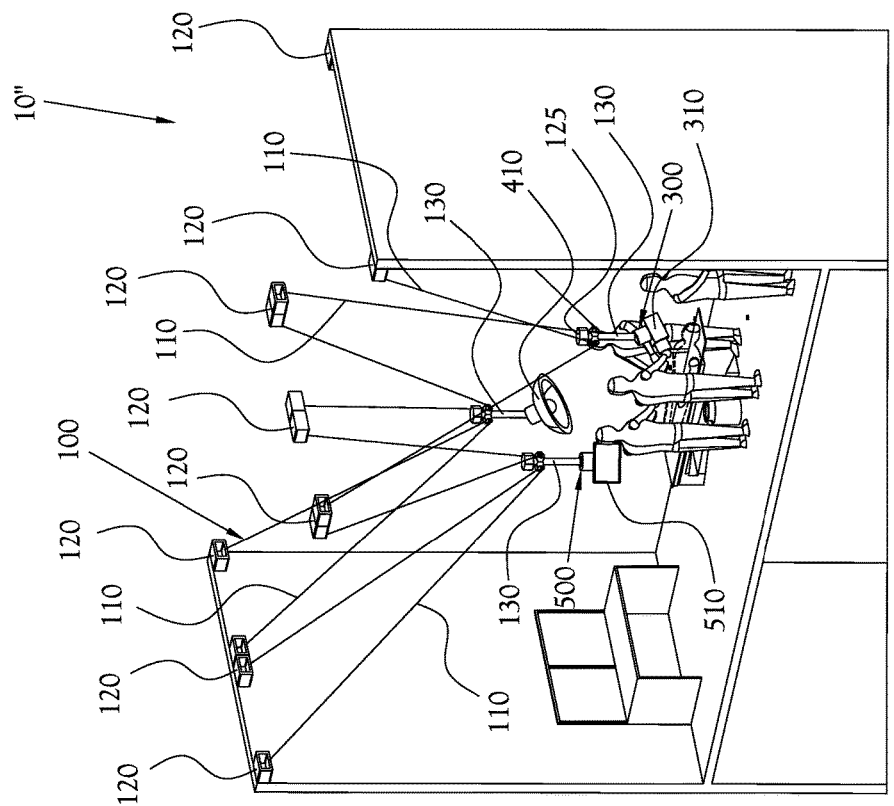
FIG. 6B is a perspective view of the exemplary embodiment system illustrated in FIG. 6A.

The cable robot module 100 of the present invention consists of three or more cables 110 and three or more motor/winch boxes 120 and performs the operations of placing the other modules, in an optimal location for monitoring activity under study, providing illumination, or transporting the requested object from point A to point B. This direction is obtained from the system's central computer 200, itself receiving information from the vector camera 310 of the imaging module 300, an integration system, and/or a variety of inputs, including manual control input, gesture recognition, voice activation, and eye or gaze tracking. The cable robot module 100 receiving this information directs the appropriate motors to reel in/out to achieve the desired location in space with, in an exemplary embodiment, six degrees of freedom, i.e. X, Y, and Z coordinates in three-dimensional space, and relative motion such as roll, pitch, and yaw. It will be appreciated that in one embodiment movement through the X, Y, and Z coordinates of three dimensional space is controlled by the winches 120 and cables 110, while relative motion such as roll, pitch, and yaw is controlled by an articulation cage 125. In a further embodiment, movement through two coordinates of three dimensional space is controlled by the winches 120 and cables 110, while movement through the third coordinate is controlled by telescoping pole 130 as best illustrated in FIGS. 4A and 4E. In performing these operations, the central computer 200 receiving real time readings from the vector camera 310 of the imaging module 300 can autonomously respond to changing atmosphere conditions to maintain an optimum line of sight for the vector camera 310 and the illumination module 400. Much the same, the cable robot can be employed for the manipulation of objects from point A to point B via direction of the central control computer module 200.

Figure 7A:
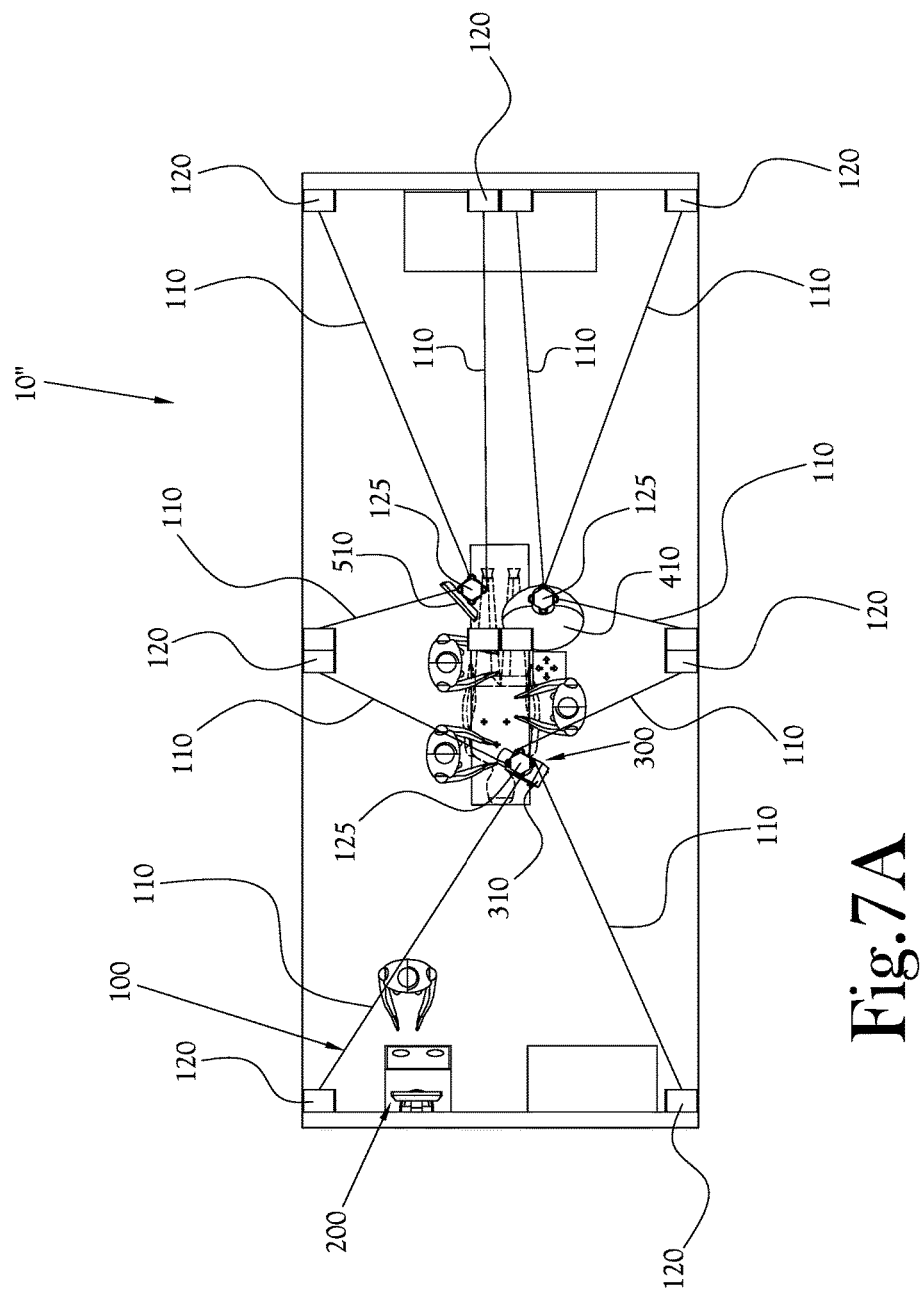
Figure 8B:
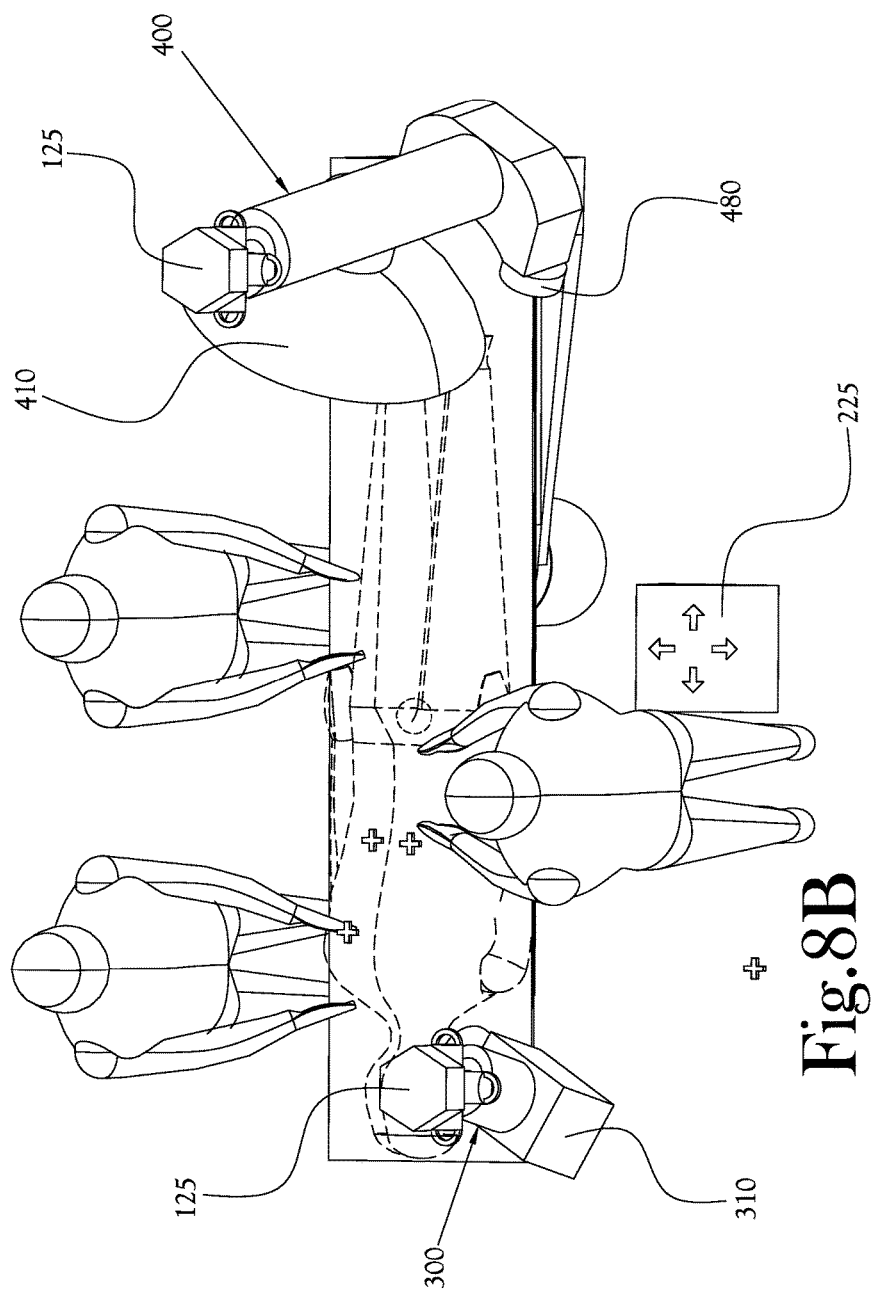
FIG. 8B is a perspective view of the embodiment illustrated in FIG. 8A and in which cables have been removed for clarity of view.
Figure 8C:
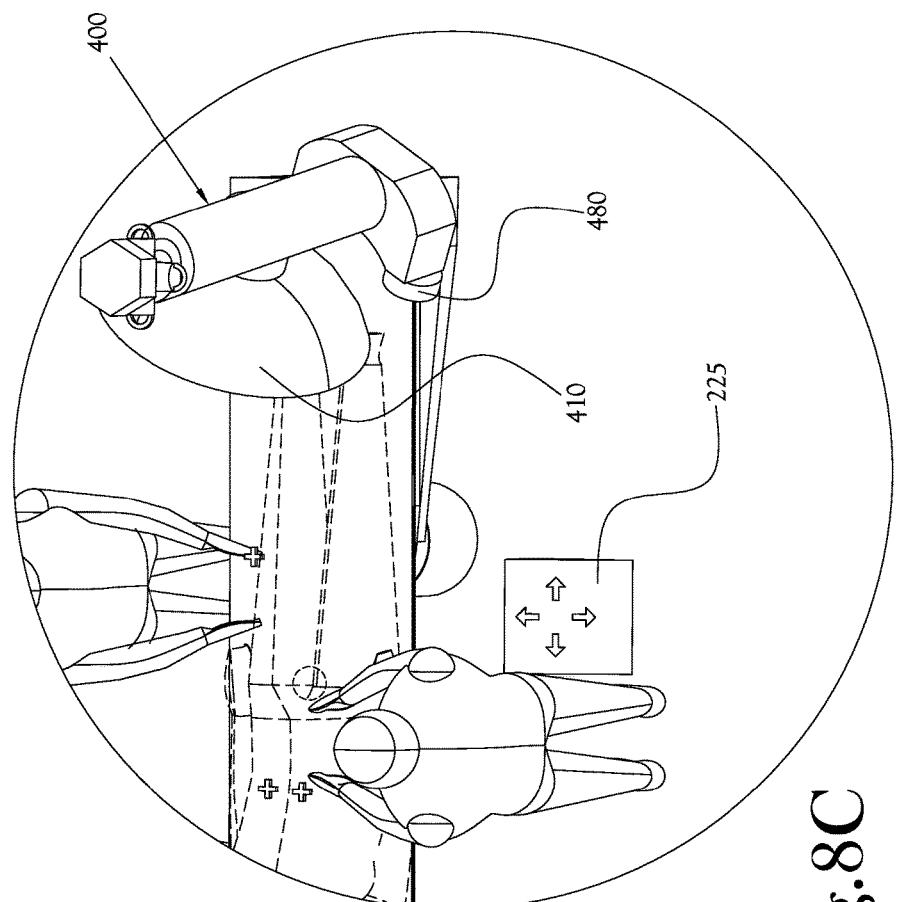
FIG. 8C is a close-up perspective view of the embodiment illustrated in FIG. 8B.
Figure 9A:
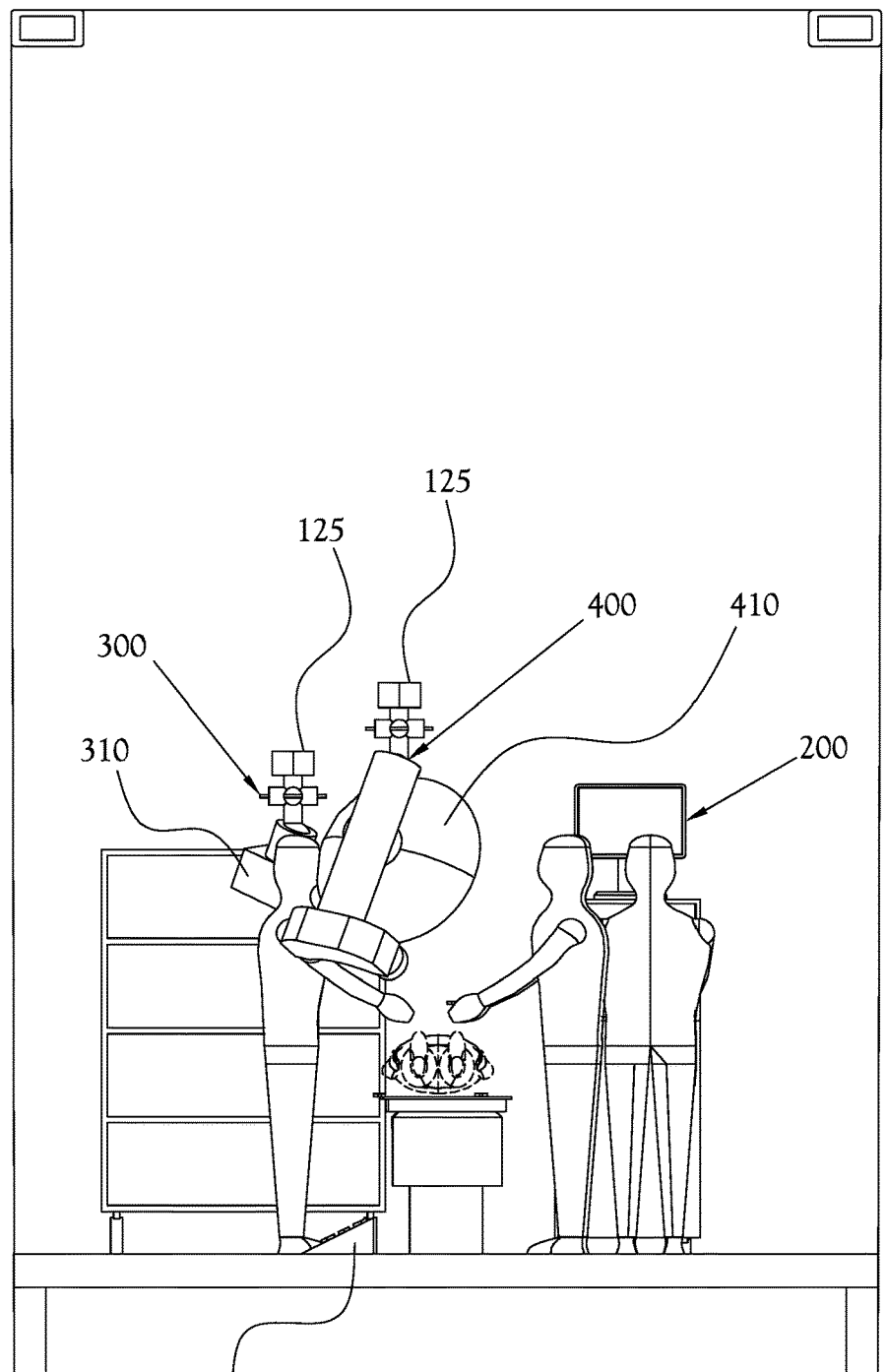
FIG. 9A is an end elevation view of the embodiment illustrated in FIG. 8A and in which cables have been removed for clarity of view.
Figure 9B:
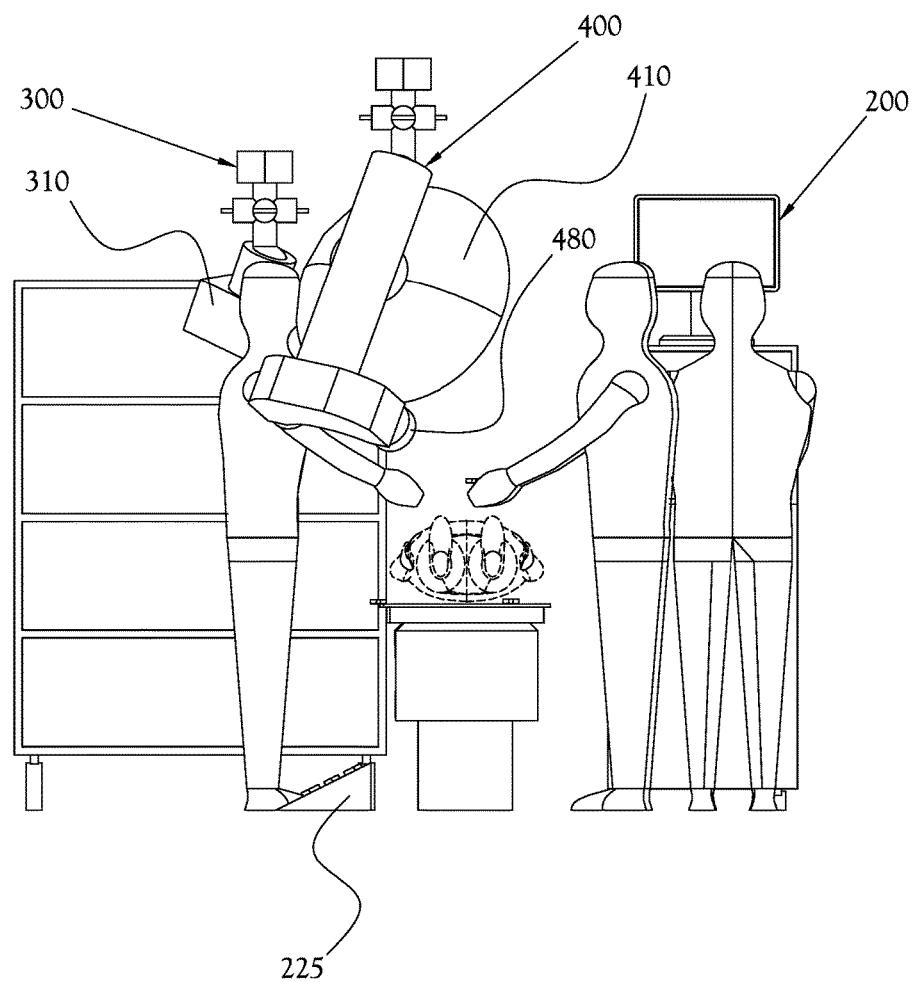
FIG. 9B is a further end elevation view of the embodiment illustrated in FIG. 8A and in which cables have been removed for clarity of view.
Figure 9C:
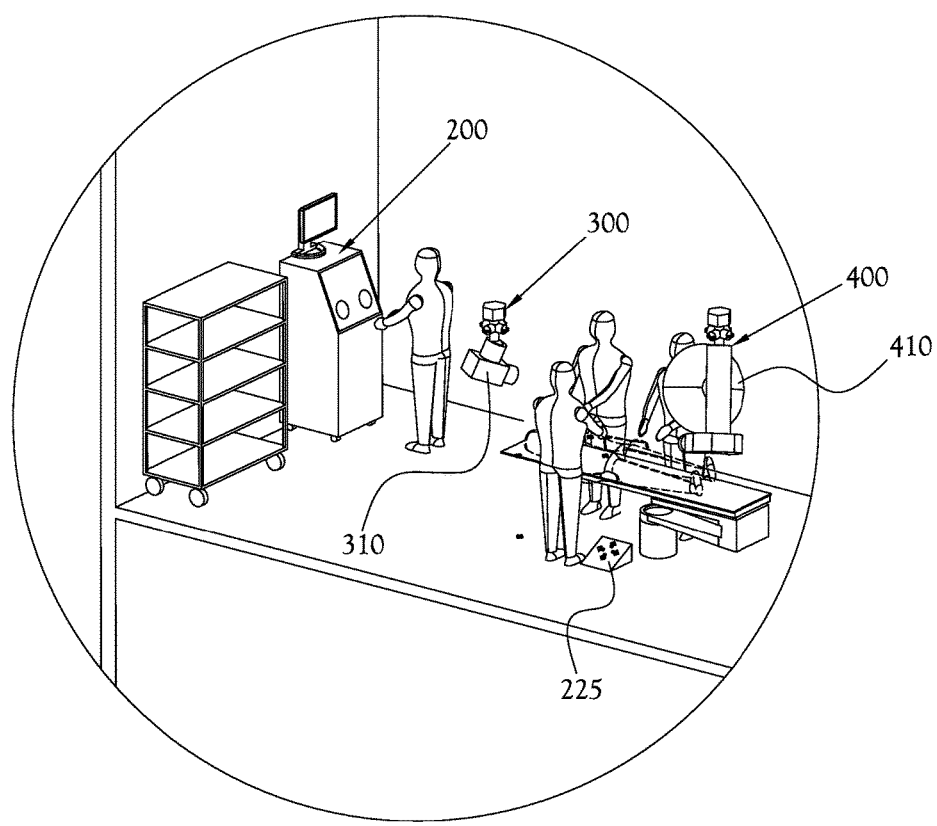
FIG. 9C is a perspective view of the embodiment illustrated in FIG. 9A and in which cables have been removed for clarity of view.

As illustrated in FIGS. 3-7B, one or more cable robot modules 100 can be provided in a given three-dimensional space. Thus, in FIG. 3, system 10 includes only one cable robot module 100. FIGS. 4A-5B, system 10' includes two robot modules 100. And, FIGS. 6A-7B, system 10" includes three robot modules 100. In this regard, it will be appreciated by those skilled in the art, that in an environment that has more than one cable robot module 100 that is active within the three-dimensional space, the system must be adapted so as to prevent entanglement or collision of the various components being carried by the individual robot modules 100. In this regard, in an exemplary embodiment, each cable robot module 100 is confined to operate within a specific zone or domain. In this regard, FIGS. 5A and 5B, and in FIGS. 7A and 7B, illustrate these separate domains for system 10', illustrated in FIGS. 5A and 5B, and system 10", illustrated in FIGS. 7A and 7B. In this regard, FIGS. 5A and 5B illustrate system 10' in which two devices are in simultaneous and independent operation and which are confined to either a first zone 135 or a second zone 145. Similarly, FIGS. 7A and 7B illustrate system 10" in which three devices are in simultaneous and independent operation and which are confined to either a first zone 135, which is similar to first zone 135 illustrated in FIG. 5B, a second zone 155 and a third zone 165. It should be appreciated by those skilled in the art, that each system 10, regardless of the number of cable robot modules 100 included within such system, system 10 will include at least one vector camera 310 as described in greater detail below.

In accordance with one exemplary embodiment, an imaging module 300 is carried and its position controlled by a cable robot module 100 described above. Various types of cameras and imaging systems can be utilized in the system of the present invention, including though not limited to: stereoscopic, infrared, ultrasound, x-ray, time of flight, wide ban, electromagnetic, laser etc. In an exemplary embodiment, system 10 includes a vector camera 310. With the assistance of the cable robot module 100 and under direction of the central control computer 200, the vector camera 310 is autonomously or manually kept within an operable range of the area of study. This is done by the vector camera's continuous monitoring of the area of interest and its surrounding to inform the central control computer 200 of its analysis and signal strength. For example, in monitoring the object of study, if the line of sight between the camera 310 and area of interest is disrupted or impeded, the vector camera 310 informs the central control computer 200 which directs the cable robot module 100 to reposition to a new location. Thus, one skilled in the art will appreciate that the devices work in tandem, synergistically, to ensure the necessary points of interest remain in the field of view of vector camera 310 to enable the production of a vector to enable the calculation of distance and angles between the points of interest. Point location can then be extracted and made relevant to the impending process via the local coordinate system of the vector camera 310 or global coordinate system of the total device. In much the same manner, the lamp 410 carried by illumination module 400 attached to the cable robot 100 maintains a clear line of sight of the area of interest via attachment to the cable robot 100. In doing this, the illumination module 400 autonomously or manually achieves a clear line of sight as described below.

Figure 10A:
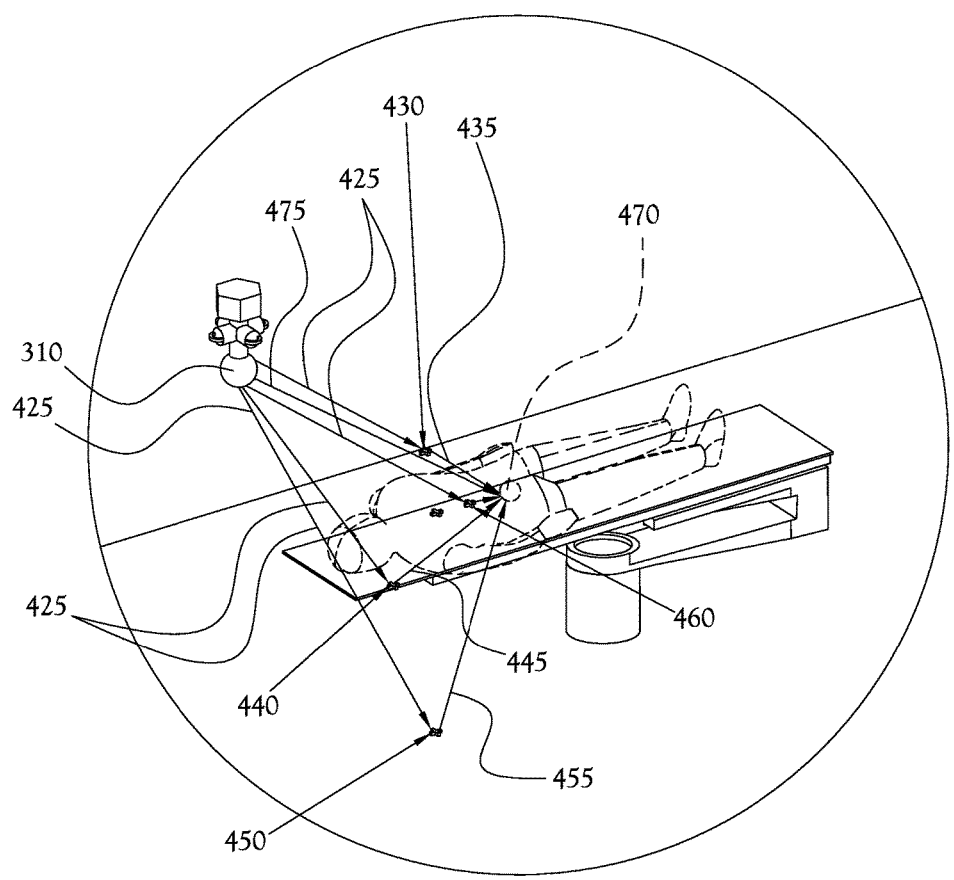
FIGS. 10A-10C are perspective, side elevation, and top plan views, respectively, illustrating the use of the vector camera of the present invention and reference markers for tracking the displacement and orientation of a marker, which in an exemplary embodiment can be attached to a surgical instrument.
Figure 10B:
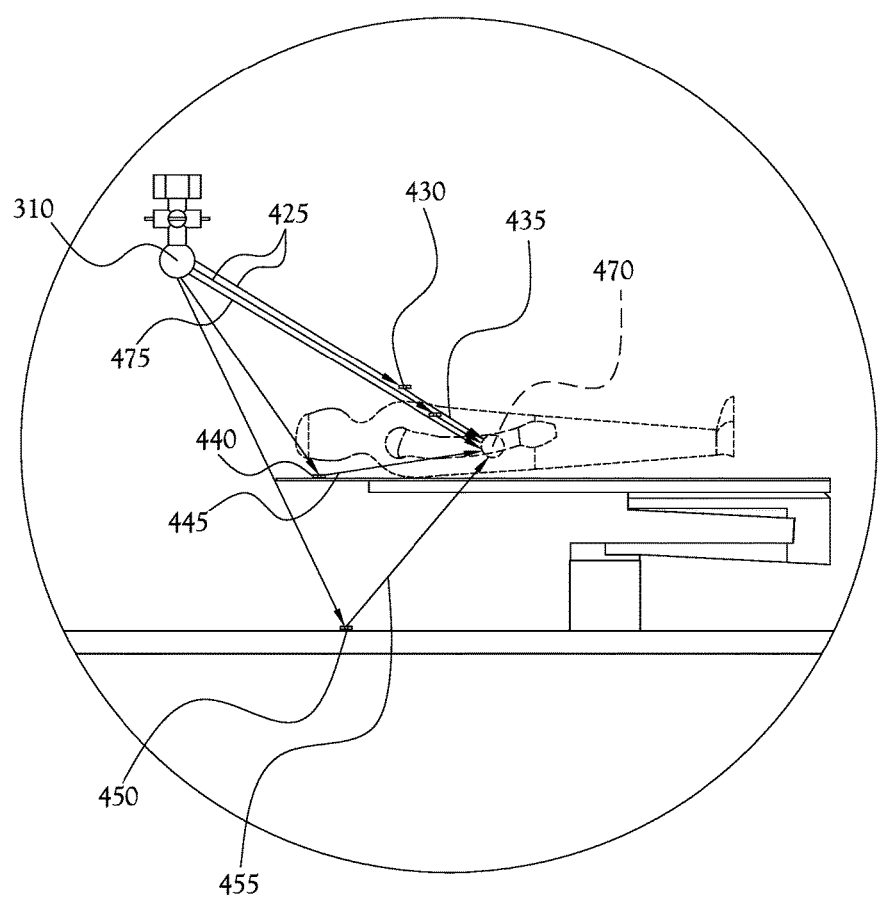
Figure 10C:
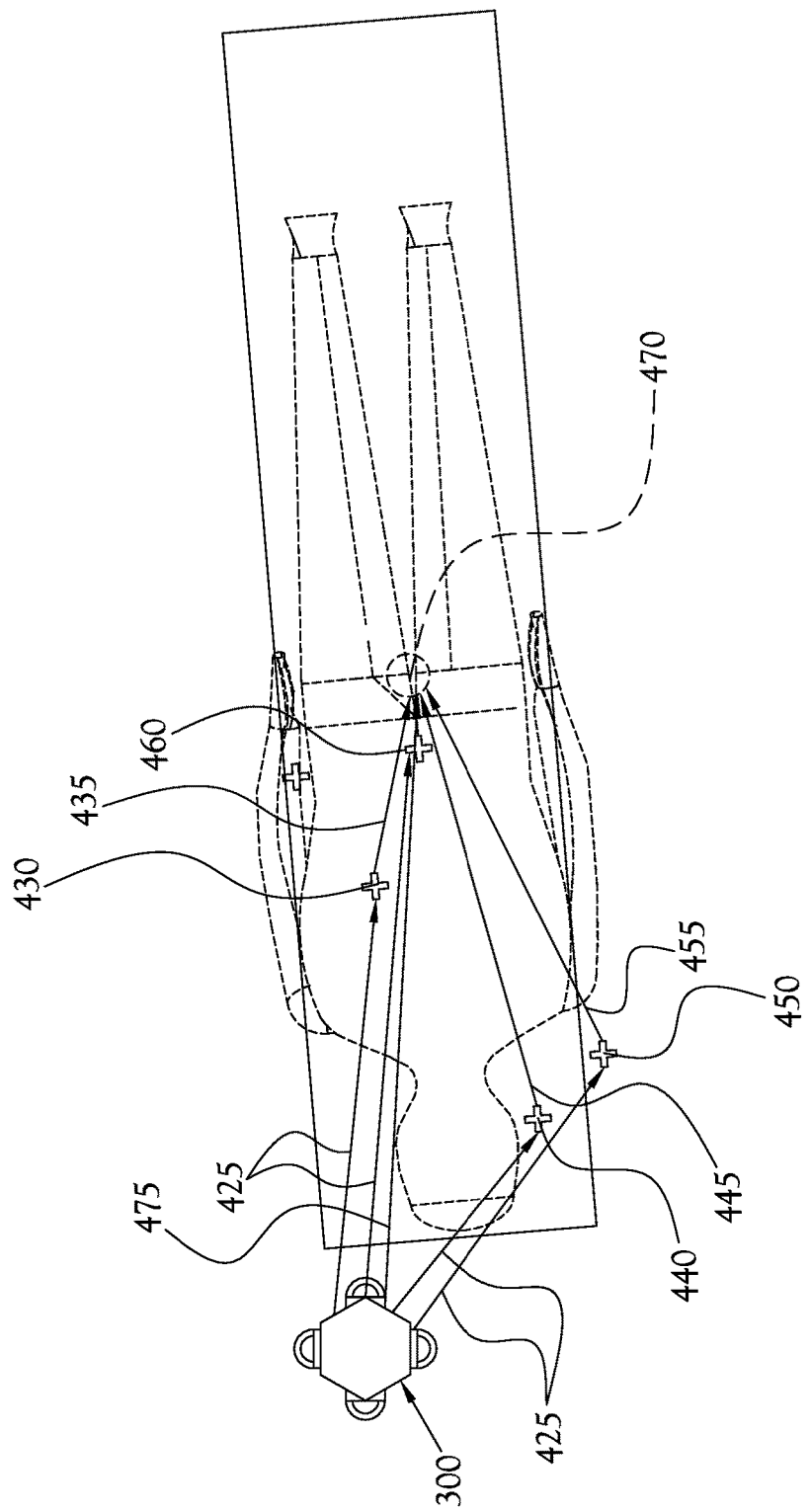

Further, referring to FIGS. 10A-10C, it can be seen that arrows 425 represent the vector from the vector camera 310 to the reference marker 430, reference marker 440, and reference marker 450 reference markers; and arrow; and that arrow 435 represents the vector from reference marker 430; arrow 445 represents the vector from reference marker 440 and arrow 455 represents the vector from reference marker 450, respectively, to the target 470 in FIGS. 10A-10C. Lastly the arrow 475 marks the vector from the vector camera 310 to the target 470 at any given time and can provide real-time feedback to clinicians as to the displacement and orientation of a marker (perhaps attached to a surgical instrument).

As mentioned above, illumination module 400, with its associated lamp 410 may also be attached to a cable robot module 100 as previously discussed. The illumination module receives control inputs from the central control computer 200 in order to deliver focused and/or ambient light to the area of study by way of information provided by the vector camera 310. For example, the cable robot module 100 receives command and control direction inputs from the central control computer 200 and may track with selected points of interest, simultaneously moving the illumination module 400 to continuously illuminate the area under study unimpeded. Similarly, changes in the environment such as glare or barrier to light may trigger the central computer module 200 to direct the cable robot module 100 to reposition the illumination module 400. Another illustration of this may be the manual input of commands, via a manual controller 225 in electronic communication, either wired or wireless electronic communication, with the central control computer 200 to redirect, reposition, refocus or further manipulate the supply of light to the area of study. In doing this, the user can be provided with a touchless means to operate illumination module 400 with six degrees of freedom.

The illumination module 400, in conjunction with the central computer module 200 and the cable robot module 100 is adapted to provide light, either as a focused spot or broad fill light to a desired area in the field of view of the imaging module 300. While this can be accomplished with a manual controller 225 described above, it will be appreciated by those skilled in the art that, in an exemplary embodiment, illumination module 400 can also be controlled by gesture control, for example the opening and spreading of the surgeon's hands and fingers for broad light or a pointed five (5) finger closing of the hand, (similar to the gesture commonly used to tell one to be silent), of the surgeon's hand for focused light. This gesture can be further commanded to the system of the present invention by pointing to a specific area using one's index finger or using one's index finger to outline (or encircle) an area of interest. Gesture control can also be used to request different modes of possible onboard light such as LED, UV, Laser or other modes of illumination. The system 10 of the present invention also provides real-time tracking and interaction with the surgical team. In this regard, by knowing the location of various team members within the operating theater and by interactively knowing where light is being requested, the system of the present invention can afford a continuous and uninterrupted source of light to the area under study, even when physical obstructions in the room (such as clinicians moving) change their position in the room. This is one example of the various components of the system of the present invention acting independently and co-dependently in order to manage workflow within the operating theater.

Further, it will be appreciated by those skilled in the art that the gesture control described herein provides the surgeon with touchless adjustment of the light within the field of view, meaning that the surgeon is not required to put their tools down in order to adjust and focus the light as needed. Moreover, as stated above, the illumination module 400 of the system 10 of the present invention can be adapted to provide different types of light sources as anticipated or as needed. In this regard, it is known that laser light is often used as a template illuminating the precise line of an incision site, thus eliminating the need to physically mark points of incision on a patient's skin. Laser light can be also used as a pointer to guide surgeon (essentially charting the path) in a way which helps them know possible underlying obstacles (bones, veins, organs) which may not be easily seen when performing incisions. This may also be combined with haptic feedback within the surgical tool to provide tactile feedback to the surgeon.

In addition to the other modules discussed herein, an object manipulator 500 may also be attached to the cable robot module 100. The object manipulator 500, being placed with six degrees of freedom in space by the cable robot 100 and under control of the central computer 200 can then be used as a means to retrieve and deliver objects, such as an auxiliary display 510, or a tool grasping mechanism, and/or manipulate them at the user's discretion. For example, the user employing the abilities of a remote foot controller 225 may direct the object manipulator module 500 to perform an operation such as open/close, engage/disengage magnetism or the like as a means to perform an action on an object separate and exterior to the object manipulator module 500.

Additionally, in an exemplary embodiment, the system 10 of the present invention can include an infrared surface thermometer 480, which can either be mounted with the vector camera 310 or as a component of the illumination module 400, and which is adapted for non-contact monitoring of temperature. In this regard, the temperature for the area of interest, either identified by the user or the system's software, can be monitored. The system is adapted to provide the user with visual, acoustic and/or haptic cues of temperature levels that fall below or rise above preset temperature levels. Further, in an exemplary embodiment, the system is adapted to warn users of component failure through the use of visual, acoustic, and/or haptic cue. In an exemplary embodiment, the system is adapted to autonomously take action to eliminate potential temperature threats based on preset software coding, actively interface with other onboard systems, implement a laser sighting apparatus to aim the infrared measurement device and mark, or show, the area under observation. In a further exemplary embodiment, the system 10 of the present invention could be adapted to function as a subsystem of a supersystem provide data and command and control information to at least one auxiliary and/or external supersystem.

EXAMPLES

In an exemplary configuration of the system 10 of the present invention, composed of a cable robot module 100 composed of four cables 110 and four motor winch boxes 120, an infrared vector camera 310, remote foot controller, touchless temperature sensor and LED lamp. The central control computer module 200 receives inputs from the onboard vector camera 310 attached to the cable robot module 100. These inputs are composed of coordinate points providing the central computer 200 with adequate information to determine the location of markers in the X, Y, and Z planes of three-dimensional space, as well as their corresponding roll, pitch and yaw. Furthermore, these inputs consist of the signal strength received by the camera from the markers allowing for the central control computer to determine when the markers become outside of the field of view of the vector camera 310. When the markers become outside the field of view of the vector camera, a switch triggers in the central control computer to activate the cable robot so as to position the vector camera in a position that brings the marks back into the vector camera's field of view.

During this activation of the cable robot, repositioning occurs placing the vector camera within range of the markers to again place the markers within the field of view of the camera. In other words, the camera monitors the markers within its field of view simultaneously receiving a signal from the markers and sending this information to the central control computer until these markers are no longer visible by the camera and therefore no longer sending a signal to the central control computer at which time a switch is triggered by the camera to the central control computer to send a signal to the cable robot to initiate repositioning. In doing this the markers are autonomously kept in range of the vector camera and therefore continuously monitored simultaneously sending location and signal strength information from the vector camera to the central control computer. When the user decides to override the autonomous tracking feature of the system, a remote control foot pedal empowers the user to reposition the cable robot by receiving a manual input from the user and converting this to an electric signal sent to the central control computer, enabling the user to place the cable robot and attached LED lamp with six degrees of freedom in space.

When the user decides to employ the LED lamp, the foot controller receives a manual input from the user and converts this input to an electronic signal which is sent to the central control computer. The central control computer then takes the signal from the foot controller and sends this to the lamp onboard the cable robot. Finally, the pyrometer performing the function of a touchless temperature sensor receives temperature readings from the area of interest. These temperature data points are sent to the central control computer where a predetermined threshold limit of 44 degrees Celsius (109.4 degrees Fahrenheit) is set. When this predetermined limit is exceeded the central control computer sends a signal to the LED lamp to decrease its intensity as well as a signal to the cable robot to reposition.

The coupling of a cable robotic system with a tool tracker or imager, as described herein, in order to synthesize into a cable driven, high precision, dynamic 6 degree-of-freedom field of view medical device for tool tracking and delivery in three dimensional space and which uses a variety of control inputs, such as manual control inputs, gesture control, voice recognition, and/or feature recognition, such as gaze tracking, in a clinical setting allows for a number of advantages over the prior art. The present invention provides for tracking of tool movement via a tracking system for monitoring the position and orientation of a tool. Further, the surgical instrument may have a unique geometry marker on one end, which in conjunction with the vector camera and control system allows the tool to be tracked. This is advantageous in situations where the utility end of the tool is out of sight to the surgeon, perhaps located within the patient's body or the tools position needs to be known with greater precision than that which can be known by the unaided human eye. The system of the present invention then knowing the vector between the marker and the tool's utility side, and, in an exemplary embodiment, in conjunction with a previously taken image of the area of study (perhaps a tumor using a CT scan) can relay the position of the tool relative to the area of interest to the surgeon through various means, including, for example, haptic feedback or visual monitoring such as on display 510.

As a further example, through the use of gesture recognition (perhaps via stereoscopic imaging) with a unique geometry marker (tracked with passive infrared markers and an infrared imager) a requested tool could be associated with a unique tool marker at location remote from the surgeon, who, by use of a designated gesture, could request the remotely located tool. The object manipulator, under control of the central control computer, then retrieves the tool and delivers it to the surgeon's outstretched, palm up hand. For instance, in one scenario, the surgeon desires a saw, which is coded as tool B within the system's software, the surgeon flashes a gesture defined as upheld two (2) fingers and places his palm upright, the system's control computer recognizes these gestures and locates tool B within the room. The object manipulator then retrieves tool B and places tool B on the surgeon's upright facing palm. Recognizing the surgeon's closed hand around the tool, the vector camera resumes its optimized observational position and tracks the tool's movement. The surgeon then completes the designated task with tool B and signals the system that he is done with tool B, by a designated gesture, in an exemplary embodiment by holding tool B upright, the system's vector camera recognizes this command, and the system activates the object manipulator to retrieve tool B and place it in a bin for sterilization.

As a further example which illustrates the synergistic combination of the multiple components of the system 10 of the present invention, a scenario is described in which two surgeons, Surgeon A and Surgeon B, begin an operation. The system of the present invention autonomously optimizes its position within the operating room to achieve the greatest viewing angle. Surgeon A begins the incision along the laser outlined line projected by the illumination control of the present system onto the patient. Needing more light to the new incision, Surgeon A uses a 5 fingered hand closing gesture & points to the incision. The vector camera visually detects this gesture and the computer control recognizes this as a command, and directs the illumination device to provide greater focused light to the incision. Surgeon B requests a scalpel, which has previously been coded as the third tool, or tool C, by flashing three fingers and holding his hand palm up. The vector camera visually detects this gesture, and the computer control recognizes this as a command, and directs the object manipulator to locate the unique geometry marker tied to tool C. The object manipulator of the present invention then retrieves tool C, a scalpel in this scenario, and places it in Surgeon B's palm up hand and begins tracking the tool's unique geometry marker using a vector to relate the tool's marker position to the utility end, as illustrated in FIGS. 10A-10C. Moreover, using a previously taken image (perhaps of a tumor using a CT scan) Surgeon B begins to operate on the patient knowing the tool's position relative to the object, or area, of interest. Upon completion of her objective, Surgeon B then holds the tool C upright, signaling the object manipulator of the system to retrieve tool C, upon which the system of the present invention recognizes the command, retrieves the tool from Surgeon B's palm and places it in a prescribed location, (such as a sterilization bin), all without requiring the surgeon to vocalize a command or take their eyes' away from the area under study.

While the present invention has been illustrated by description of several embodiments and while the illustrative embodiments have been described in detail, it is not the intention of the applicant to restrict or in any way limit the scope of the appended claims to such detail. Additional modifications will readily appear to those skilled in the art. The invention in its broader aspects is therefore not limited to the specific details, representative apparatus and methods, and illustrative examples shown and described. Accordingly, departures may be made from such details without departing from the spirit or scope of applicant's general inventive concept.

Having thus described the aforementioned invention, what is claimed is:

1. A system adapted for controlling light, for moving and tracking tools in three dimensional space through at least six degrees of freedom, said system comprising:
a cable robot module having a plurality of cables, winches and motors, said cable robot module adapted to move an object through X, Y, and Z coordinates of three-dimensional space, said cable robot module further including an articulation cage adapted for attachment to said object and further adapted to control roll, pitch, and yaw of said object;
a central computer module in electronic communication with said cable robot module and adapted for receiving inputs and providing command and control signals to said cable robot module; and
an imaging module carried by said cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system.

2. The system of claim 1 wherein said system further comprises an illumination module carried by said cable robot module, said illumination module being in electronic communication with said central computer module, wherein said illumination module includes a lamp having a luminous output controlled by said central computer module.

3. The system of claim 1 wherein said system further comprises an object manipulator module carried by said cable robot module, said object manipulator module being in electronic communication with and under control of said central computer module.

4. The system of claim 1 wherein an illumination module in electronic communication with said central computer module is carried by a further cable robot module.

5. The system of claim 1 wherein an object manipulator module in electronic communication with said central computer module is carried by a further cable robot module.

6. The system of claim 3 wherein said object manipulator module is adapted to grasp and release a selected object and is further adapted to deliver said selected object to a user, track relative position and orientation of said selected object, and retrieve said selected object from said user.

7. The system of claim 1 wherein said central computer module is adapted to receive manual inputs from a manual controller and is further adapted for feature recognition, gesture recognition, gaze tracking and voice control.

8. The system of claim 1 wherein said system further comprises at least one touchless temperature sensor.

9. The system of claim 1 wherein said system is adapted to provide information and control functions to at least one auxiliary, external supersystem.

10. A system adapted for controlling light, for moving and tracking tools in three dimensional space through at least six degrees of freedom, said system comprising:
a robot module having a plurality of cables, winches and motors, said cable robot module adapted to move an object through X, Y, and Z coordinates of three-dimensional space, said cable robot module further including an articulation cage adapted for attachment to said object and further adapted to control roll, pitch, and yaw of said object;
a central computer module in electronic communication with said cable robot module and adapted for receiving inputs and providing command and control signals to said cable robot module;
an imaging module carried by said cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system; and an illumination module carried by said cable robot module, said illumination module being in electronic communication with said central computer module, wherein said illumination module includes a lamp having a luminous output controlled by said central computer module.

11. The system of claim 10 wherein said system further comprises an object manipulator module carried by said cable robot module, said object manipulator module being in electronic communication with and under control of said central computer module.

12. The system of claim 10 wherein an object manipulator module in electronic communication with said central computer module is carried by a further cable robot module.

13. The system of claim 10 wherein said object manipulator module is adapted to grasp and release a selected object and is further adapted to deliver said selected object to a user, track relative position and orientation of said selected object, and retrieve said selected object from said user.

14. The system of claim 11 wherein said central computer module is adapted to receive manual inputs from a manual controller and is further adapted for feature recognition, gesture recognition, gaze tracking and voice control.

15. The system of claim 10 wherein said system further comprises at least one touchless temperature sensor.

16. The system of claim 10 wherein said system is adapted to provide information and control functions to at least one auxiliary, external supersystem.

17. A system adapted for controlling light, for moving and tracking tools in three dimensional space through at least six degrees of freedom, said system comprising:
a cable robot module having a plurality of cables, winches and motors, said cable robot module adapted to move an object through X, Y, and Z coordinates of three-dimensional space, said cable robot module further including an articulation cage adapted for attachment to said object and further adapted to control roll, pitch, and yaw of said object;
a central computer module in electronic communication with said cable robot module and adapted for receiving inputs and providing command and control signals to said cable robot module;
an imaging module carried by said cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system; and
an object manipulator module in electronic communication with said central computer module, said object manipulator being adapted to deliver a selected tool to a user, track relative position and orientation of said selected tool, and retrieve said selected tool from said user based upon data generated by said vector camera.

18. The system of claim 17 wherein said system further comprises an illumination module carried by said cable robot module, said illumination module being in electronic communication with said central computer module, wherein said illumination module includes a lamp having a luminous output controlled by said central computer module.

19. The system of claim 17 wherein an illumination module in electronic communication with said central computer module is carried by a further cable robot module.

20. The system of claim 17 wherein said central computer module is adapted to receive manual inputs from a manual controller and is further adapted for feature recognition, gesture recognition, gaze tracking and voice control.

21. The system of claim 17 wherein said system further comprises at least one touchless temperature sensor.

22. The system of claim 17 wherein said object manipulator module is adapted to grasp and release a selected object.

23. The system of claim 17 wherein said system is adapted to provide information and control functions to at least one auxiliary, external supersystem.

24. A system adapted for controlling light, for moving and tracking tools in three dimensional space through at least six degrees of freedom, said system comprising:
a cable robot module having a plurality of cables, winches and motors, said cable robot module adapted to move an object through X, Y, and Z coordinates of three-dimensional space, said cable robot module further including an articulation cage adapted for attachment to said object and further adapted to control roll, pitch, and yaw of said object;
a central computer module in electronic communication with said cable robot module and adapted for receiving inputs and providing command and control signals to said cable robot module;
an imaging module carried by said cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system;
an object manipulator module in electronic communication with said central computer module, said object manipulator being adapted to grasp and release a selected object and is further adapted to deliver said selected object to a user, track relative position and orientation of said selected object, and retrieve said selected object from said user based upon data generated by said vector camera; and
an illumination module carried by said cable robot module, said illumination module being in electronic communication with said central computer module, wherein said illumination module includes a lamp having a luminous output controlled by said central computer module.

25. The system of claim 24 wherein said central computer module is adapted to receive manual inputs from a manual controller and is further adapted for feature recognition, gesture recognition, gaze tracking and voice control.

26. The system of claim 24 wherein said system further comprises at least one touchless temperature sensor.

27. The system of claim 24 wherein said object manipulator module is adapted to grasp and release a selected object.

28. The system of claim 24 wherein said system is adapted to provide information and control functions to at least one auxiliary, external supersystem.

29. A system adapted for controlling light, for moving and tracking tools in three dimensional space through at least six degrees of freedom, said system comprising:
at least a first cable robot module having a plurality of cables, winches and motors, said first cable robot module adapted to move an object through X, Y, and Z coordinates of three-dimensional space, said first cable robot module further including an articulation cage adapted for attachment to said object and further adapted to control roll, pitch, and yaw of said object;

a central computer module in electronic communication with said first cable robot module and adapted for receiving inputs and providing command and control signals to said first cable robot module; and an imaging module carried by said first cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system.

30. The system of claim 29 wherein said system further comprises an illumination module carried by a second cable robot module, said second cable robot module being in electronic communication with said central computer module, said illumination module being in electronic communication with said central computer module, wherein said illumination module includes a lamp having a luminous output controlled by said central computer module.

31. The system of claim 29 wherein said system further comprises an object manipulator module carried by a second cable robot module, said second cable robot module being in electronic communication with said central computer module, said object manipulator module being in electronic communication with and under control of said central computer module.

32. The system of claim 30 wherein said system further comprises an object manipulator module carried by a third cable robot module, said third cable robot module being in electronic communication with said central computer module, said object manipulator module being in electronic communication with and under control of said central computer module.

33. The system of claim 31 wherein said object manipulator module is adapted to grasp and release a selected object and is further adapted to deliver said selected object to a user, track relative position and orientation of said selected object, and retrieve said selected object from said user.

34. The system of claim 29 wherein said central computer module is adapted to receive manual inputs from a manual controller and is further adapted for feature recognition, gesture recognition, gaze tracking and voice control.

35. The system of claim 29 wherein said system further comprises at least one touchless temperature sensor.

36. The system of claim 29 wherein said system is adapted to provide information and control functions to at least one auxiliary, external supersystem.

37. A system adapted for controlling light, for moving and tracking tools in three dimensional space through at least six degrees of freedom, said system comprising:

a cable robot module having a plurality of cables, winches and motors, wherein said cables and winches move an object through two coordinates of three-dimensional space, said cable robot module further including an articulation cage adapted for attachment to said object and further adapted to control roll, pitch, and yaw of said object said cable robot further including a telescoping pole adapted to move said object through a third coordinate of three-dimensional space;

a central computer module in electronic communication with said cable robot module and adapted for receiving inputs and providing command and control signals to said cable robot module; and an imaging module carried by said cable robot module, said imaging module including a vector camera in electronic communication with said central computer module, said vector camera being adapted to identify at least two markers located within a field of view of said vector camera, and further wherein said vector camera is adapted to measure data, including an angle and a distance from one selected marker to a further selected marker, and communicating said data to said the central computer module for direction of said system.

38. The system of claim 37 wherein said system further comprises an illumination module carried by said cable robot module, said illumination module being in electronic communication with said central computer module, wherein said illumination module includes a lamp having a luminous output controlled by said central computer module.

39. The system of claim 37 wherein said system further comprises an object manipulator module carried by said cable robot module, said object manipulator module being in electronic communication with and under control of said central computer module.

40. The system of claim 37 wherein an illumination module in electronic communication with said central computer module is carried by a further cable robot module.

41. The system of claim 37 wherein an object manipulator module in electronic communication with said central computer module is carried by a further cable robot module.

42. The system of claim 39 wherein said object manipulator module is adapted to grasp and release a selected object and is further adapted to deliver said selected object to a user, track relative position and orientation of said selected object, and retrieve said selected object from said user.

43. The system of claim 37 wherein said central computer module is adapted to receive manual inputs from a manual controller and is further adapted for feature recognition, gesture recognition, gaze tracking and voice control.

44. The system of claim 37 wherein said system further comprises at least one touchless temperature sensor.

45. The system of claim 37 wherein said system is adapted to provide information and control functions to at least one auxiliary, external supersystem.

46. The system of claim 38 wherein said system further comprises an object manipulator module carried by said cable robot module, said object manipulator module being in electronic communication with and under control of said central computer module.

* * * * *